(12) United States Patent
Dhanotiya et al.

(10) Patent No.: US 12,702,407 B2
(45) Date of Patent: Aug. 11, 2026

(54) ACTUATORS FOR MEDICAL DEVICES AND RELATED SYSTEMS AND METHODS

(71) Applicants: Boston Scientific Scimed, Inc., Maple Grove, MN (US); Boston Scientific Medical Device Limited, Galway (IE)

(72) Inventors: Aditya Dhanotiya, Indore (IN); Nabarun Bhowmick, Kolkata (IN); James Weldon, Newton, MA (US); Shrikant Vasant Raut, Mumbai (IN)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 429 days.

(21) Appl. No.: 18/319,661

(22) Filed: May 18, 2023

(65) Prior Publication Data

US 2023/0404573 A1 Dec. 21, 2023

Related U.S. Application Data

(60) Provisional application No. 63/344,236, filed on May 20, 2022.

(51) Int. Cl.

| | |
|---|---|
| ***A61B 17/00*** | (2006.01) |
| ***A61B 17/068*** | (2006.01) |
| ***A61B 90/00*** | (2016.01) |

(52) U.S. Cl.
CPC .......... *A61B 17/068* (2013.01); *A61B 90/361* (2016.02); *A61B 2017/00398* (2013.01); *A61B 2017/0046* (2013.01)

(58) Field of Classification Search
CPC ......... A61B 17/00; A61B 2017/00367–00473; A61B 34/70
See application file for complete search history.

(56) References Cited

U.S. PATENT DOCUMENTS

2020/0288944 A1 9/2020 Narayana et al.
2021/0095753 A1 4/2021 Uchida et al.

FOREIGN PATENT DOCUMENTS

JP S59 105435 A 6/1984
JP S59 197229 A 11/1984

*Primary Examiner* — Lynsey C Eiseman
(74) *Attorney, Agent, or Firm* — Bookoff McAndrews, PLLC

(57) ABSTRACT

According to an example, a handle assembly for a medical device may comprise a handle body, and a first knob for controlling movement of a distal portion of the medical device, the first knob may comprise a first rotational axis, and a second knob for controlling movement of the distal portion of the medical device, the second knob may comprise a second rotational axis, wherein the first rotational axis may be spaced from the second rotational axis.

15 Claims, 16 Drawing Sheets

412
477
423
424
427
426
442
444
470
425
440
422

448
412
477
420
446

422
423
477
424
446
420

422
448
425
423
440
442
412
427
426
424
444
446
420

442
423
414
440
422
426
444
424
450
456
452
481
454
460
458
490
420

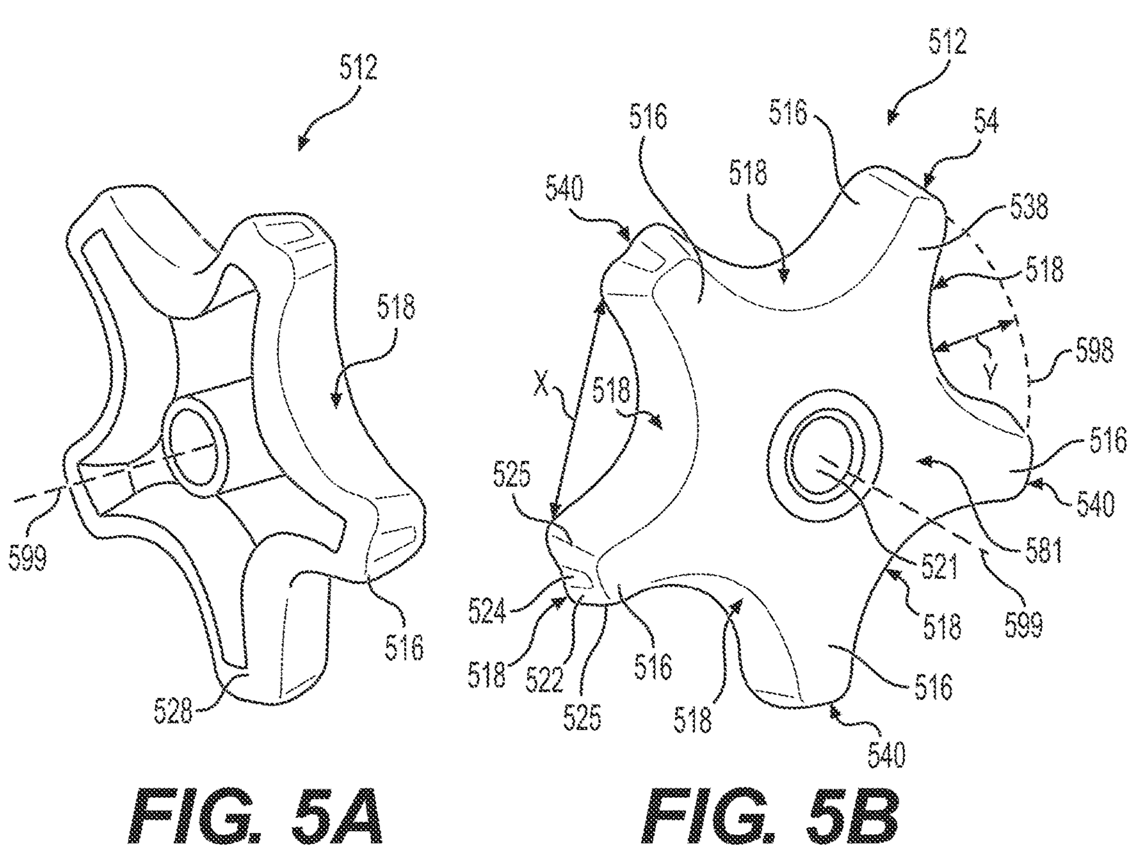
FIG. 5A
FIG. 5B
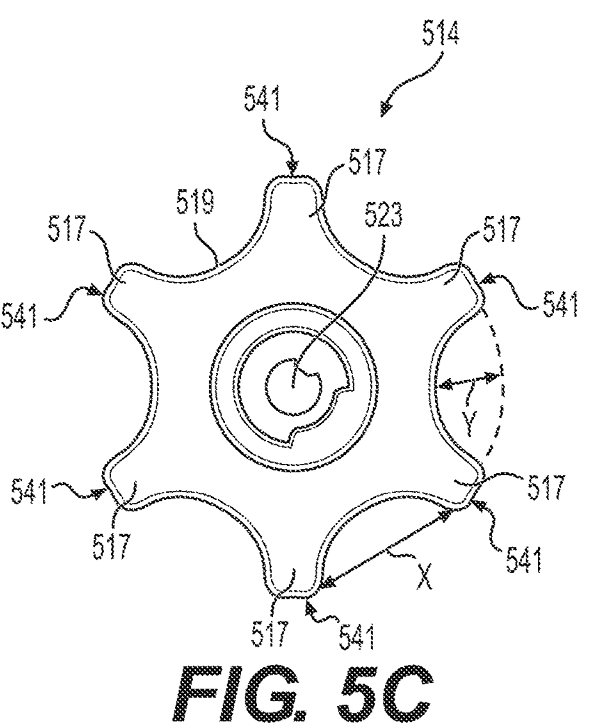
FIG. 5C
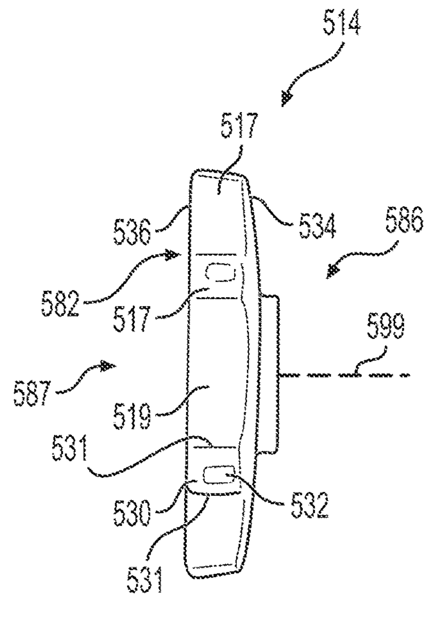
FIG. 5D

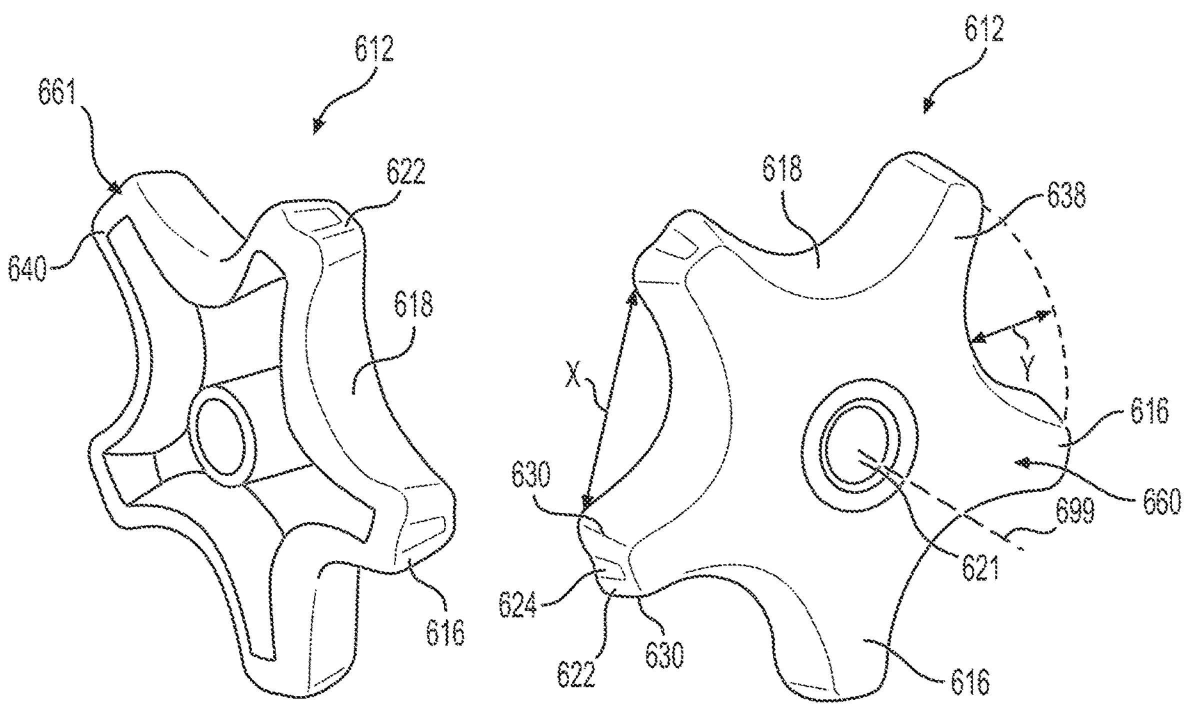
FIG. 6A
FIG. 6B
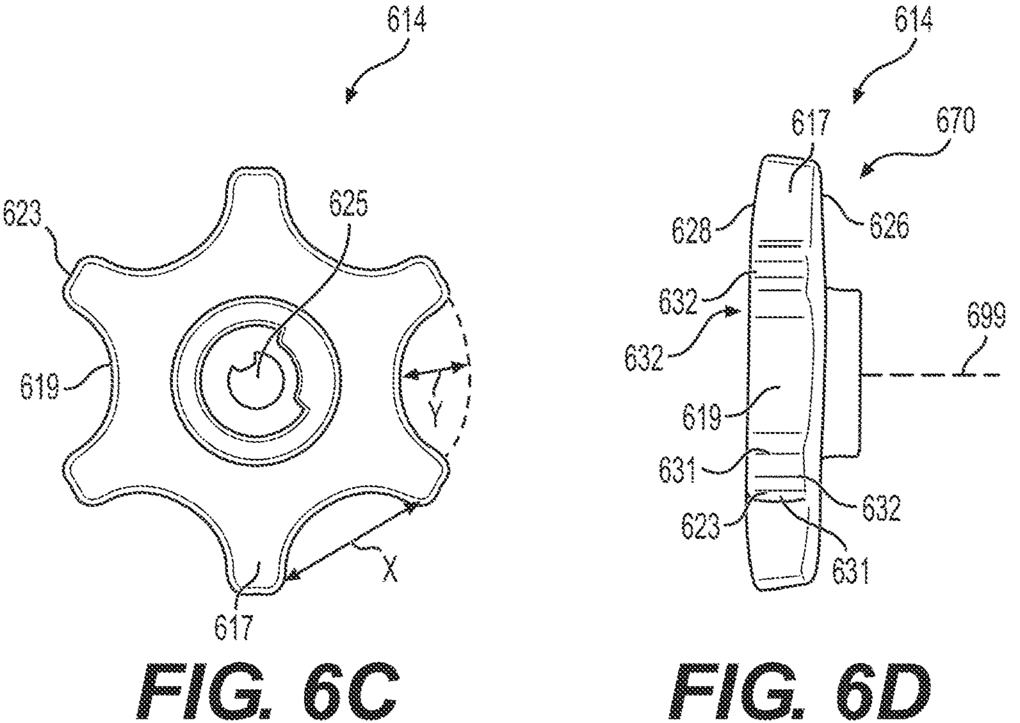
FIG. 6C
FIG. 6D

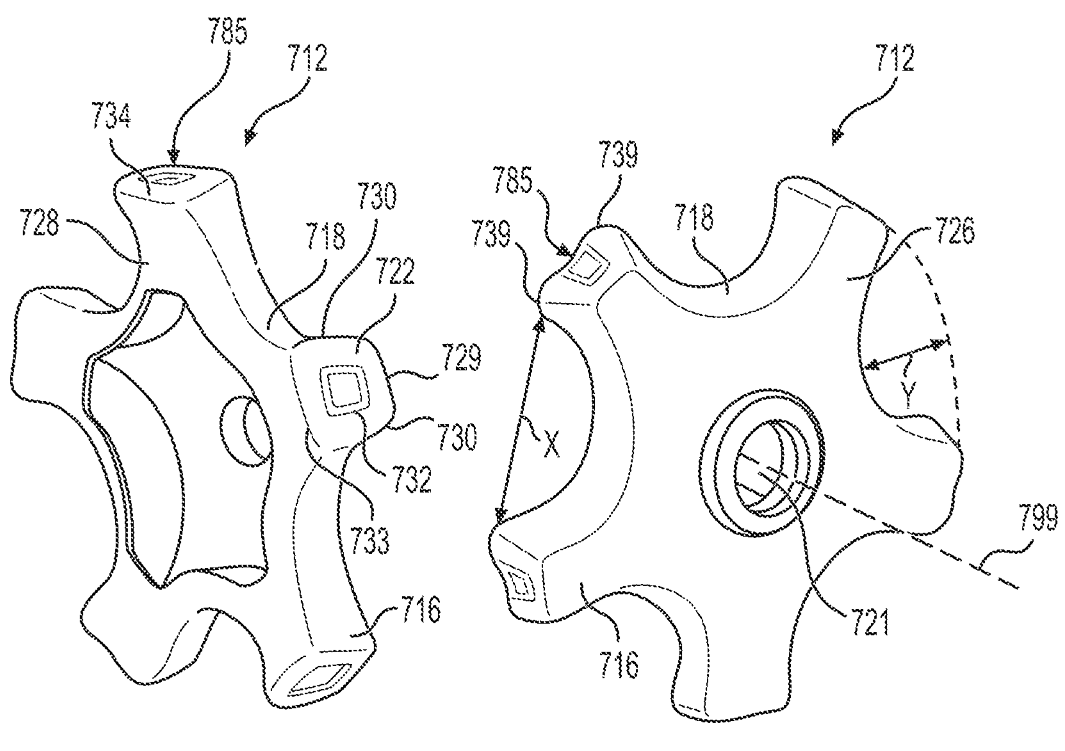
FIG. 7A FIG. 7B
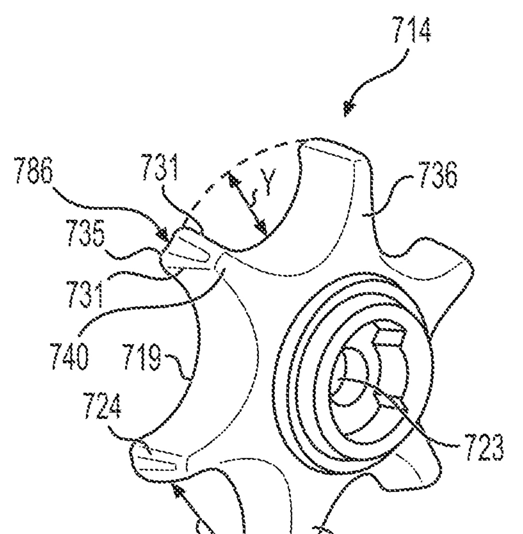
FIG. 7C
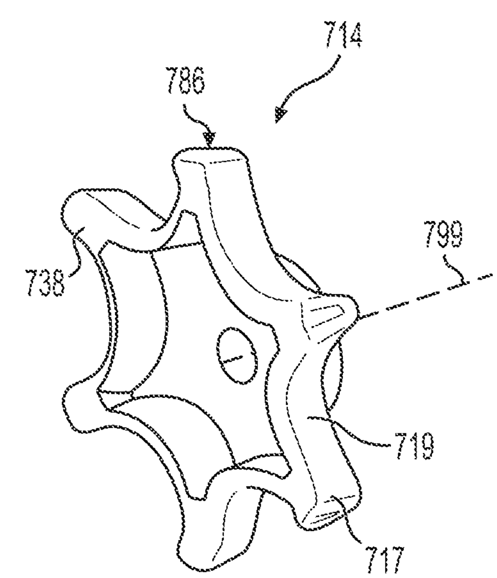
FIG. 7D

ACTUATORS FOR MEDICAL DEVICES AND RELATED SYSTEMS AND METHODS

CROSS-REFERENCE TO RELATED APPLICATIONS

This application claims the benefit of priority under 35 U.S.C. § 119 from U.S. Provisional Application No. 63/344,236, filed May 20, 2022, which is incorporated by reference herein in its entirety.

TECHNICAL FIELD

Various aspects of this disclosure relate generally to actuators of medical devices. More specifically, embodiments of this disclosure relate to ergonomic actuators for an endoscope or other medical device, among other aspects.

BACKGROUND

During endoscopic procedures, the medical professional operating the endoscope often wraps his/her entire palm around a grip or handle portion of the device. Various actuators on the handle of the endoscope require the medical professional to contort his/her hands frequently and for prolonged periods of time during a procedure, which can cause strain, or even an injury. In some cases, actuation of different scope controls, like knobs or an elevator, may result in excessive movements of the medical professional's thumb or other fingers, which may result in strain in the medical professional's hand. Endoscope operators can experience wrist and hand discomfort resulting from holding and manipulating the endoscope's handle, and repetitive hand adjustments to access various actuators on the handle. In some cases, medical professionals may experience symptoms similar to those of Carpal Tunnel Syndrome, tendonitis, or De Quervain's tenosynovitis. When a medical professional experiences fatigue or other pain in the fingers, hand, or wrist, the medical professional may shift from a primary grip position to a secondary grip position that may be a less powerful grip than the primary grip position, such as shifting from a four finger grip to a three finger grip. Repeatedly reaching or contorting the fingers to access various actuators can increase fatigue or other pain.

When a medical professional repeatedly readjusts his or her hand grip in between procedure tasks, the procedure may be prolonged and procedural tasks may be more difficult. Depending on the size of a medical professional's hand, actuators may be positioned in non-optimized positions and increase the number of readjustments of the professional's hand during a procedure. For example, a medical professional with smaller hands may have difficulty reaching control knobs of an endoscope, while simultaneously holding the grip of the endoscope, for example.

SUMMARY

According to an example, a handle assembly for a medical device may comprise a handle body, and a first knob for controlling movement of a distal portion of the medical device, the first knob rotatable about a first rotational axis, and a second knob for controlling movement of the distal portion of the medical device, the second knob rotatable about a second rotational axis, wherein the first rotational axis may be offset from the second rotational axis.

In another example, the first knob may taper towards the first rotational axis as the first knob extends away from the handle body. The second knob may taper towards the second rotational axis as the second knob extends towards the handle body. The first knob may include grip protrusions extending radially outward, relative to the first rotational axis, from a radially outward facing surface of the first knob. The first rotational axis may be substantially parallel to the second rotational axis. The medical device may further comprise a gearing assembly configured to rotate a first actuation shaft offset from the second rotational axis when the second knob rotates about the second rotational axis. The gearing assembly may be contained within a casing positioned between the first knob and the second knob. The gearing assembly may include a first gear fixedly coupled to the second knob, a second gear fixedly coupled to the first actuation shaft, and a third gear engaged with the first gear and the second gear. The medical device may further comprise a second actuation shaft configured to rotate about the first rotational axis when the first knob rotates. The first actuation shaft may rotate about the first rotational axis. The second rotational axis may be spaced approximately ten millimeters from the first rotational axis. The handle body may include a first side and a second side opposite from the first side, wherein each of the first knob and the second knob are positioned on the first side. A radially outermost surface, relative to the first rotational axis, of the first knob may be spaced from the first rotational axis approximately the same distance as a radially outermost surface, relative to the second rotational axis, of the second knob is spaced from the first rotational axis. The first knob may include a series of radial projections, and each radial projection may include a recessed portion at a tip of the respective radial projection. In some examples, a gearing assembly may comprise a first gear coupled to the second knob, a second gear coupled to a first actuation shaft, and a third gear configured to engage with the first gear and the second gear.

According to an example, a handle assembly for a medical device may comprise a handle body, a first knob for controlling movement of a distal portion of the medical device, the first knob rotatable about a first rotational axis, a second knob for controlling movement of the distal portion of the medical device, the second knob rotatable about a second rotational axis, and a gear assembly that may be configured to rotate a first actuation shaft when the second knob rotates, wherein the first actuation shaft may rotate about the first rotational axis, and wherein the second knob may be offset from the first knob. Each of the first knob and the second knob may include radial projections, and each of the radial projections may curve towards the handle body. Each of the first knob and the second knob may include radial projections, and each of the radial projections may include a triangular shaped tip portion. Each of the first knob and the second knob include radial projections, wherein the radial projections of the first knob may curve towards the handle body and the radial projections of the second knob may curve away from the handle body. The gearing assembly may comprise a first gear coupled to the second knob, a second gear coupled to the first actuation shaft, and a third gear configured to engage with the first gear and the second gear.

According to an example, a method of operating a medical device that may include a handle and a shaft extending longitudinally from the handle, may comprise rotating a first knob of the handle about a first rotation axis relative to the handle to move a portion of the shaft in a first direction and rotating a second knob of the handle about a second rotation axis relative to the handle to move the portion of the shaft in a second direction, wherein the second direction may be different from the first direction, and wherein the first rotation axis is spaced from the second rotation axis.

BRIEF DESCRIPTION OF THE DRAWINGS

The accompanying drawings, which are incorporated in and constitute a part of this specification, illustrate exemplary aspects of this disclosure and together with the description, serve to explain the principles of the disclosure.

FIGS. 5A-5D are perspective views of exemplary control knobs, according to aspects of this disclosure.

FIGS. 6A-6D are perspective views of exemplary control knobs, according to aspects of this disclosure.

FIGS. 7A-7D are perspective views of exemplary control knobs, according to aspects of this disclosure.

DETAILED DESCRIPTION

Reference will now be made in detail to aspects of this disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. Throughout the figures included in this application, arrows labeled "P" and "D" are used to show the proximal and distal directions in the figure. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Further, relative terms such as, for example, "about," "substantially," "approximately," etc., are used to indicate a possible variation of ±10% in a stated numeric value or range.

Embodiments of this disclosure seek to improve a user's ability to grip, manipulate, and otherwise apply force to a handle, and actuators of the handle, of a medical device, such as an endoscope, during a medical procedure. Embodiments of this disclosure may help reduce the need to reposition a user's hand during a procedure, reduce strain to a user's hand from excessive movement of fingers or uncomfortable positioning of fingers, and maximize muscle strength during operation of a medical device, among other aspects.

Figures 1A, 1B:
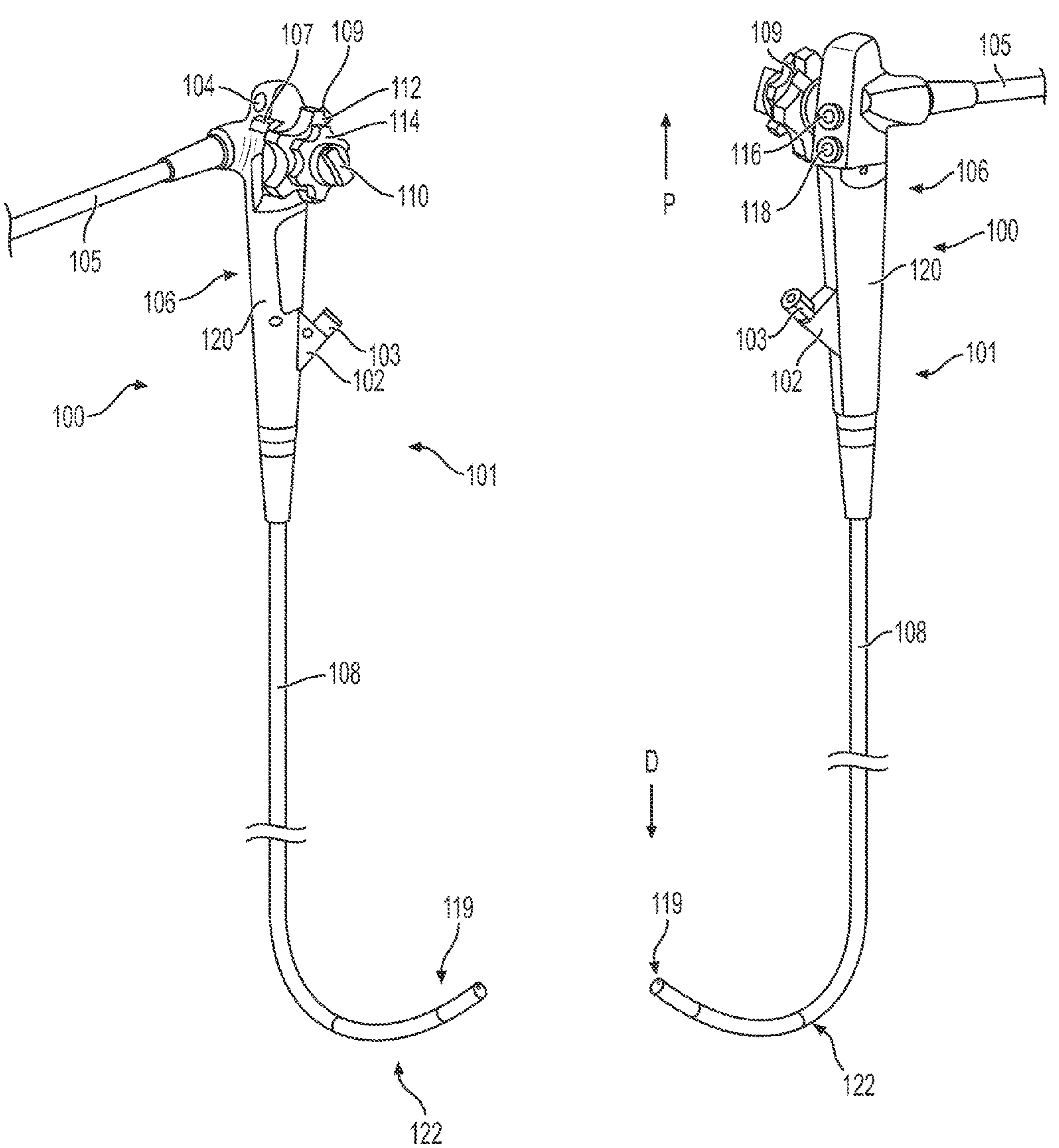
FIGS. 1A and 1B are perspective views of an exemplary endoscope, according to aspects of this disclosure.

FIGS. 1A and 1B show a perspective view of an exemplary endoscope system 100 including an endoscope 101. Endoscope 101 may include a handle assembly 106 and a flexible tubular shaft 108. The handle assembly 106 may include a biopsy port 102, a biopsy cap 103, an image capture button 104, an elevator actuator 107, a first locking lever 109, a second locking lever 110, a first control knob 112, a second control knob 114, a suction button 116, an air/water button 118, a handle body 120, and an umbilicus 105. All of the actuators, elevators, knobs, buttons, levers, ports, or caps of endoscope system 100 may serve any purpose and are not limited by any particular use that may be implied by the respective naming of each component used herein. The umbilicus 105 may extend from handle body 120 to auxiliary devices, such as a control unit, water supply, or vacuum source. The umbilicus 105 therefore can transmit signals between the endoscope 101 and the control unit, to control lighting and imaging components of the endoscope 101 and/or receive image data from the endoscope 101. The umbilicus 105 also can provide fluid for irrigation from the water supply and/or suction to a distal tip 119 of the shaft 108. The buttons 116 and 118 control valves for suction and fluid supply, respectively. The shaft 108 may terminate at the distal tip 119. The shaft 108 may include an articulation section 122 for deflecting the distal tip 119 in up, down, left, and/or right directions. The knobs 112 and 114 may be used for controlling such deflection, and the locking levers 109 and 110 may lock the knobs 112 and 114, respectively, in desired positions. The handle body 120 may be tapered and may narrow as the handle extends distally such that the profile of the handle body 120 is smaller at its distal end than at its proximal end.

The distal tip 119 may include an imaging device (e.g., a camera) and a lighting source (e.g., an LED or an optical fiber). The distal tip 119 may be side-facing. That is, imaging device and lighting source may face radially outward, perpendicularly, approximately perpendicularly, or otherwise transverse to a longitudinal axis of the shaft 108 and the distal tip 119.

Although the term endoscope may be used herein, it will be appreciated that other devices, including, but not limited to, duodenoscopes, colonoscopes, ureteroscopes, bronchoscopes, laparoscopes, sheaths, catheters, or any other suitable delivery device or medical device may be used in connection with the devices of this disclosure.

In operating endoscope system 100, a user may use his/her left hand to hold the handle assembly 106 (shown in FIG. 2A) while the right hand is used to hold accessory devices and/or operate one or more of the actuators of the handle assembly 106, such as the first and second control knobs 112, 114 and the first and second locking levers 109, 110. The user may grasp the handle assembly 106 by wrapping the user's hand around the handle body 120. When grasping handle body 120, the user may use the left thumb to operate the first and second control knobs 112, 114 and the elevator actuator 107 (through rotation about their axis), and may use a left-hand finger to operate the image capture button 104, the suction button 116, and the air/water button 118 (each by pressing).

Figures 2A, 2B:
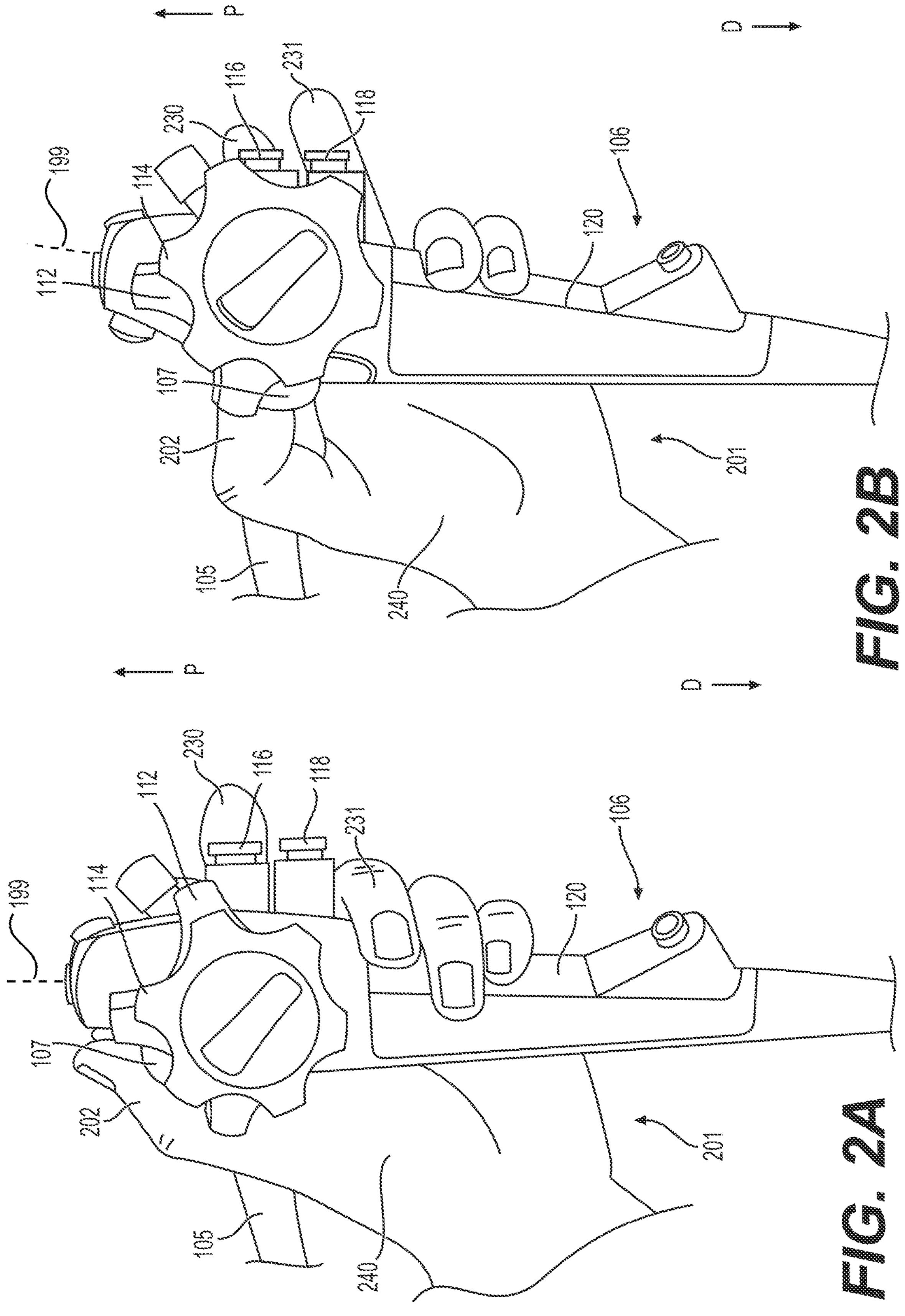
FIGS. 2A and 2B are perspective views of a user's hand holding an endoscope handle, according to aspects of this disclosure.

FIGS. 2A and 2B show an exemplary user's left hand 201 grasping handle assembly 106. The user's left index finger 230 and middle finger 231 may be used to operate the suction button 116 and the air/water button 118. A user may have to reach and/or strain their index or middle finger to actuate the suction button 116 and/or the air water button 118. A user may have to reach and/or strain their left thumb and/or hold their left thumb in uncomfortable positions to operate the first and second control knobs 112, 114, and/or the elevator actuator 107. The actuators and handle assemblies discussed herein below may help reduce the desired reach and/or alleviate strain to a user's fingers and/or hand. Handle assembly 106 may have a central longitudinal axis 199 extending longitudinally through handle assembly 106.

The user may position the thumb 202 of the grasping hand 201 over the elevator actuator 107 and move the elevator actuator 107 along a circular path from a first position (shown in FIG. 2A) to a second position (shown in FIG. 2B) by moving the thumb 202. As shown in FIG. 2B, the palm 240 may move away from the handle body 120 when the thumb 202 moves from the first position to the second position, and a user may have difficulty reaching the suction button 116 and/or the air water button 118 with the index or middle fingers when the palm 240 moves away from the handle body 120. In some examples, a user may actuate the first and second control knobs 112, 114 using the thumb 202, and the user may need to reach and potentially strain the thumb 202 to actuate the control knob 114. The actuators and handle assemblies discussed herein below may help reduce the movement required of the index and/or other fingers to actuate the suction button 116 and/or the air water button 118, and may reduce the movement required of the thumb to actuate the first and second control knobs 112, 114 or other actuator during operation of the endoscope 101.

Figure 3:
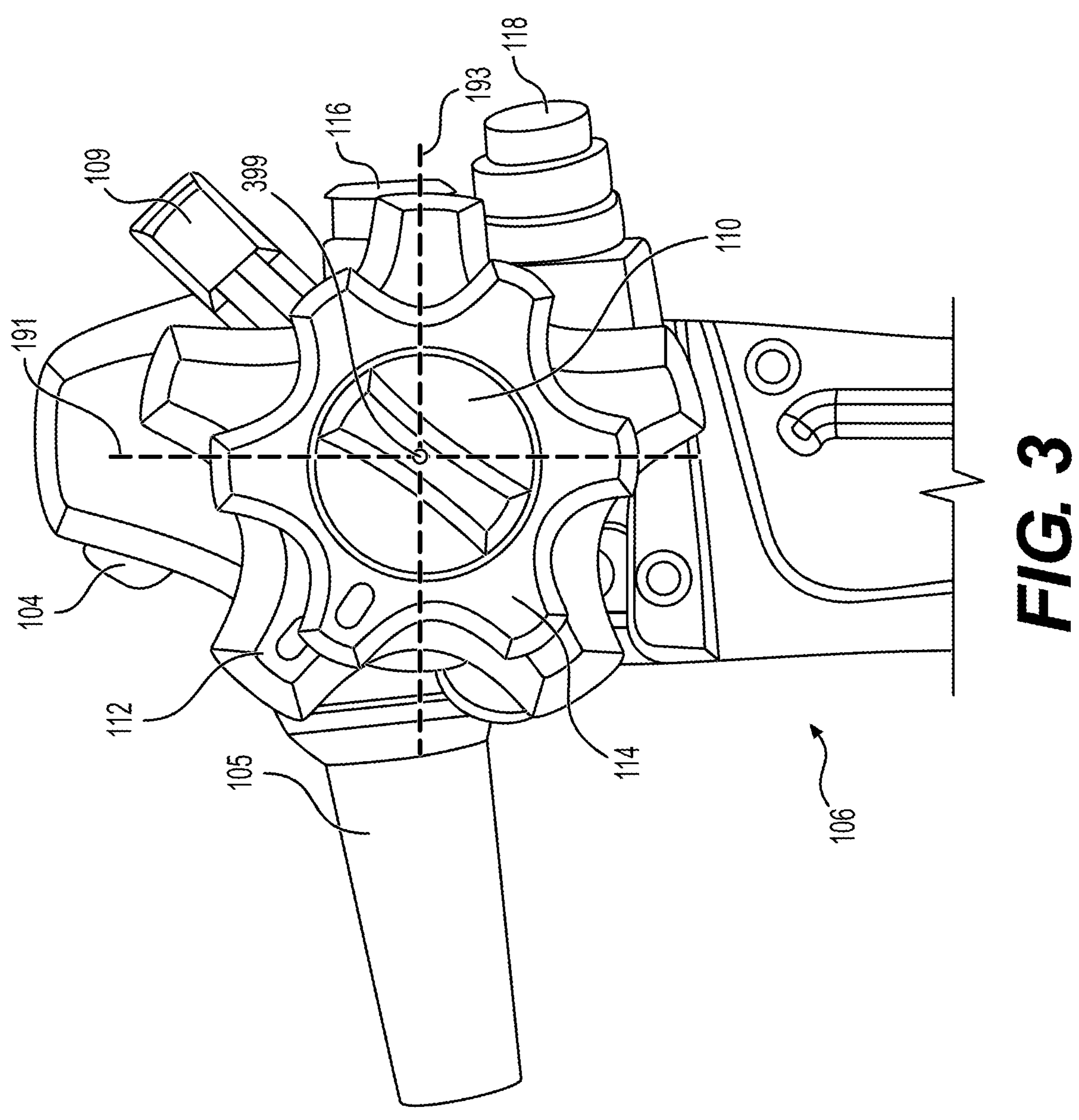
FIG. 3 is a side view of a proximal portion of an exemplary handle assembly, according to aspects of this disclosure.

As shown in FIG. 3, conventional control knobs 112 and 114 of endoscope 101 are coaxial. In other words, the control knobs 112 and 114 have a common rotational axis 399 that extends through the center of the typical control knobs 112 and 114, shown extending through the page in FIG. 3. Control knob 112 has a central longitudinal axis and a central horizontal axis that are parallel to a central longitudinal axis 191 and a central horizontal axis 193 of the control knob 114, respectively. The coaxial arrangement of control knobs 112 and 114 may limit access of the user's thumb 202 to the control knob 114. For example, a portion of the user's thumb 202 may be positioned within a recess of the control knob 112, and the user may be required to reach and/or strain thumb 202 in order to actuate control knob 114.

Figure 4A:
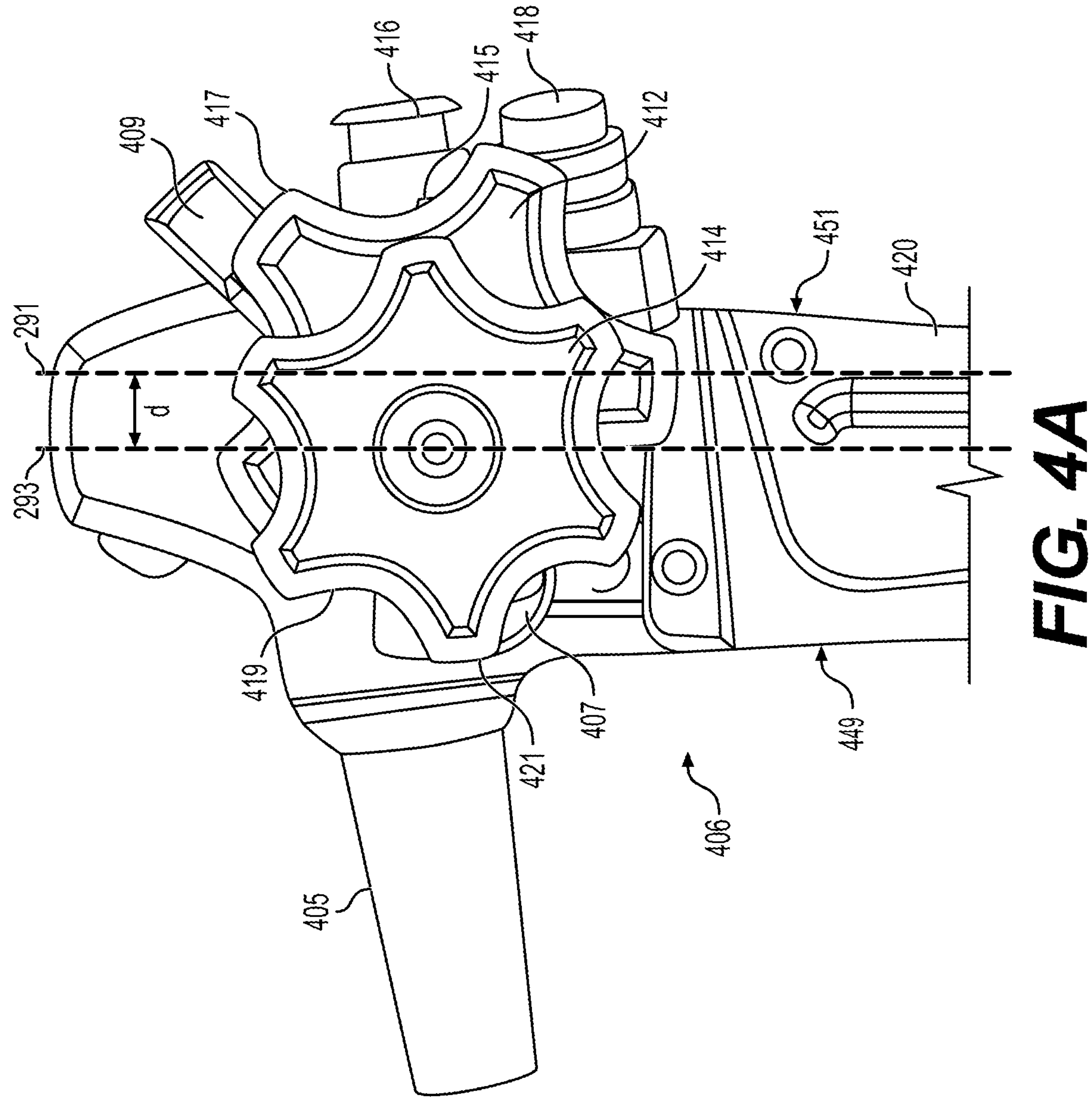
FIGS. 4A and 4B are side and top views, respectively, of an exemplary handle assembly, according to aspects of this disclosure.
Figure 4B:
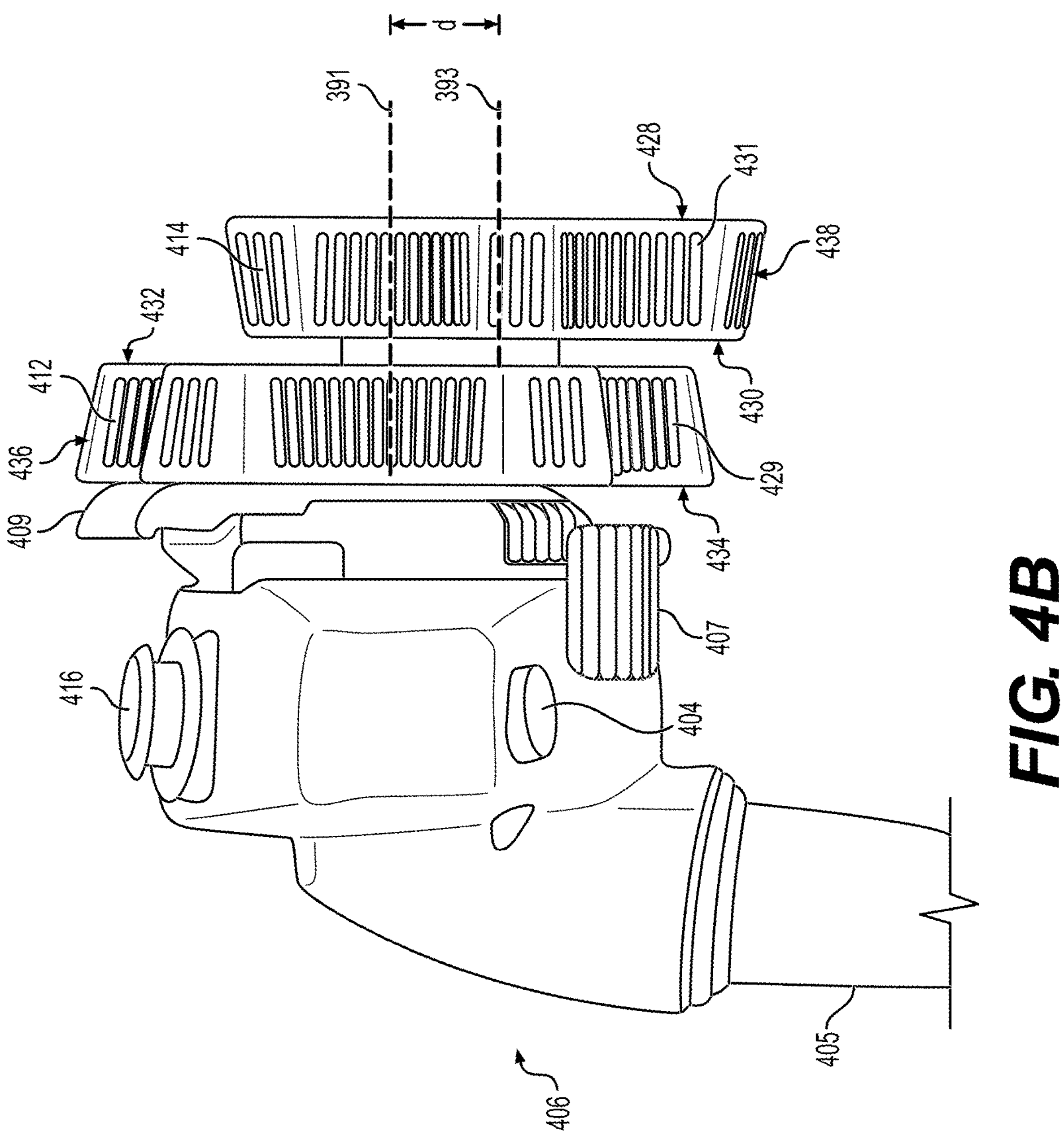
Figure 4C:
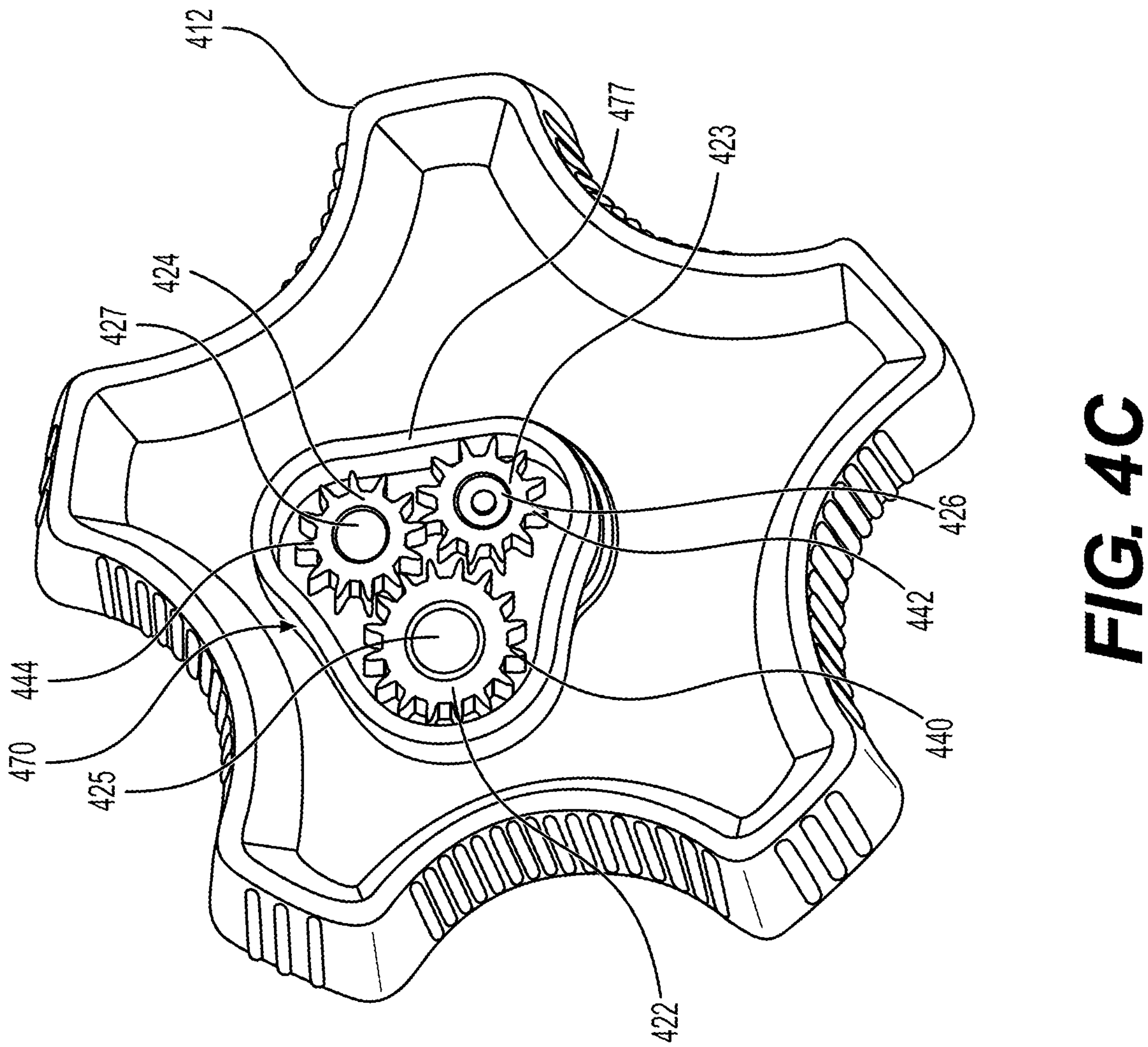
FIGS. 4C-4G are various perspective views of portions of the exemplary knob mechanism for the handle assembly in FIGS. 4A and 4B, with various portions removed to expose interior portions of the knob mechanism, according to aspects of this disclosure.

FIGS. 4A and 4B are top and side views of an exemplary handle assembly 406. Handle assembly 406 may have the same or similar structure and function as like elements of handle assembly 106. Specifically, an image capture button 404, an umbilicus 405, an elevator actuator 407, a first locking lever 409, a suction button 416, and an air/water button 418, are the same or similar to the image capture button 104, the umbilicus 105, the elevator actuator 107, the first locking lever 109, the suction button 116, and the air/water button 118. The handle assembly 406 further includes a first control knob 412 and a second control knob 414 with similar function as the first control knob 112 and the second control knob 414. The first control knob 412 includes alternating radial protrusions 417 and recesses 415 spaced circumferentially from one another, and form a continuous surface 436. The second control knob 414 includes alternating radial protrusions 421 and recesses 419 spaced circumferentially from one another, and form a continuous surface 438. Handle body 420 may include a first side 449 and a second side 451 positioned on an opposite side of handle body 420 from first side 449.

The first control knob 412 may have a central longitudinal axis 291 and the second control knob 414 may have a central longitudinal axis 293 that are spaced apart by a distance d such that the control knobs 412 and 414 do not share a common rotational axis. As shown in FIG. 4B, first control knob 412 rotates about a rotational axis 391 and the second control knob 414 rotates about a rotational axis 393. The distance d between the central longitudinal axis 291 of the first control knob 412 and the central longitudinal axis 293 of the second control knob 414 may be approximately 10 (ten) millimeters. In some examples, distance d between the central longitudinal axis 291 of the first control knob 412 and the central longitudinal axis 293 of the second control knob 414 may be between 1 millimeter and 50 millimeters (inclusive). Positioning of the second control knob 414 closer to first side 449 of the handle body 420 may position control knob 414 closer to a user's thumb during operation, and thus may allow a user to more easily access and/or reach the second control knob 414 with his or her thumb. Shifting the position of the second control knob 414 closer to a first side 449 of the handle body 420 may also allow the user to operate control knobs 412, 414 with one hand, for example, the left hand, rather than both hands.

Referring to FIG. 4B, the surface 436 extends from a first side 434 of the first control knob 412 to a second side 432 of the first control knob 412. The surface 436 is angled relative to rotational axis 391 of first control knob 412, and in some examples may extend towards rotational axis 391 as surface 436 extends away from the handle body 420 (as shown in FIG. 4B). The surface 438 of second control knob 414 extends from a first side 428 of the second control knob 414 to a second side 430 of the second control knob 414. The surface 438 is angled relative to rotational axis 393 of second control knob 414, and in some examples may extend towards rotational axis 393 as surface 438 extends towards handle body 420 (as shown in FIG. 4B).

A diameter of first side 434 of the first control knob 412 is greater than a diameter of second side of the first control knob 412. A diameter of first side 428 of the second control knob 414 is greater than the diameter of second side 430 of the second control knob 414. Since surface 438 extends towards rotational axis 393 as surface 438 extends towards handle body 120, this angled configuration may facilitate a user's thumb 202 contacting surface 438 when operating the second control knob 414.

The surfaces 436, 438 of control knobs 412, 414 may include grip projections 429, 431, respectively (e.g., radial grip projections), to improve gripping capabilities. Each grip projection 429, 431 protrudes from adjacent portions of the outer surface 438 having the grip projection 429, 431. Each grip projection 429, 431 may be extend across surface 438 substantially parallel to rotational axis 393 and may extend radially outward from rotational axis 393.

FIGS. 4C-4F illustrate a gear mechanism 470 incorporated into control knobs 412, 414. The gear mechanism 470 may be used to transmit motion of control knob 414 to the distal tip 119. The gear mechanism 470 may include a first gear 422 with external teeth 440 fixedly coupled to the second control knob 414, a first shaft 425 fixedly coupled to a casing 477 and rotatably coupled to the first gear 422, a second gear 423 with external teeth 442, a second shaft 426 fixedly coupled to the second gear 423, and an idle gear 424 with external teeth 444 arranged to engage the external teeth 440 of the first gear 422 and the external teeth 442 of the second gear 423. The idle gear 424 is rotatably coupled to a third shaft 427, and the third shaft 427 is fixedly coupled to the casing 477. The second shaft 426 extends through the first control knob 412 and into the handle body 420 to an internal gear assembly 480 (shown in FIGS. 4G and 4I). The gears 422, 423, 424 and portions of the shafts 425, 426, 427 may be enclosed/contained within the casing 477, and the casing 477 may be positioned between the first control knob 412 and the second control knob 414. A mounting support 446 may extend from the casing 477, through an arch shaped opening 448 of the first control knob 412, and to the handle body 420 The mounting support 446 fixedly couples the casing 477 to the handle body 420. The mounting support may be integral with handle body 420 and may be offset from knob axis 391. The opening 448 surrounds a portion of the shaft 426. The opening 448 allows for the first control knob 412 to rotate without interference from the mounting support 446. For example, as a user rotates the first control 412 about the rotational axis 391, the opening 448 moves relative to the fixed mounting support 446. In some examples, opening 448 may limit rotation of first control knob 412 to less than 360 degrees in either direction, such as limit rotation to approximately 180 degrees. The mounting support 446 may be cylindrical in shape and positioned adjacent to a portion of the shaft 426. When a user rotates the second control knob 414, the mounting support 446 and the casing 477 remain fixed, while the gears 422, 423, 424 and second control knob 414 rotate.

Figures 4D, 4E, 4F, 4G:
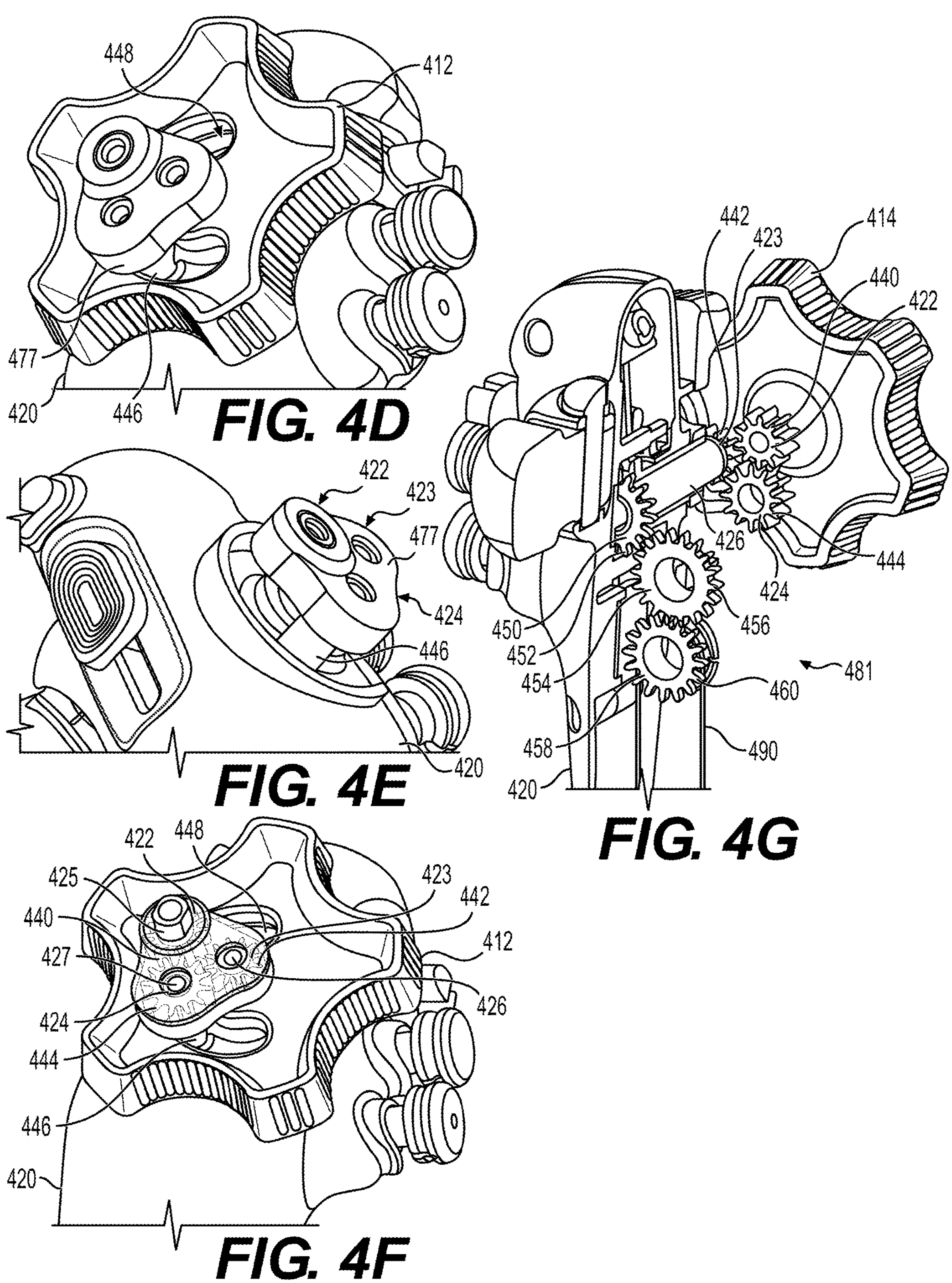
Figures 4H, 4I:
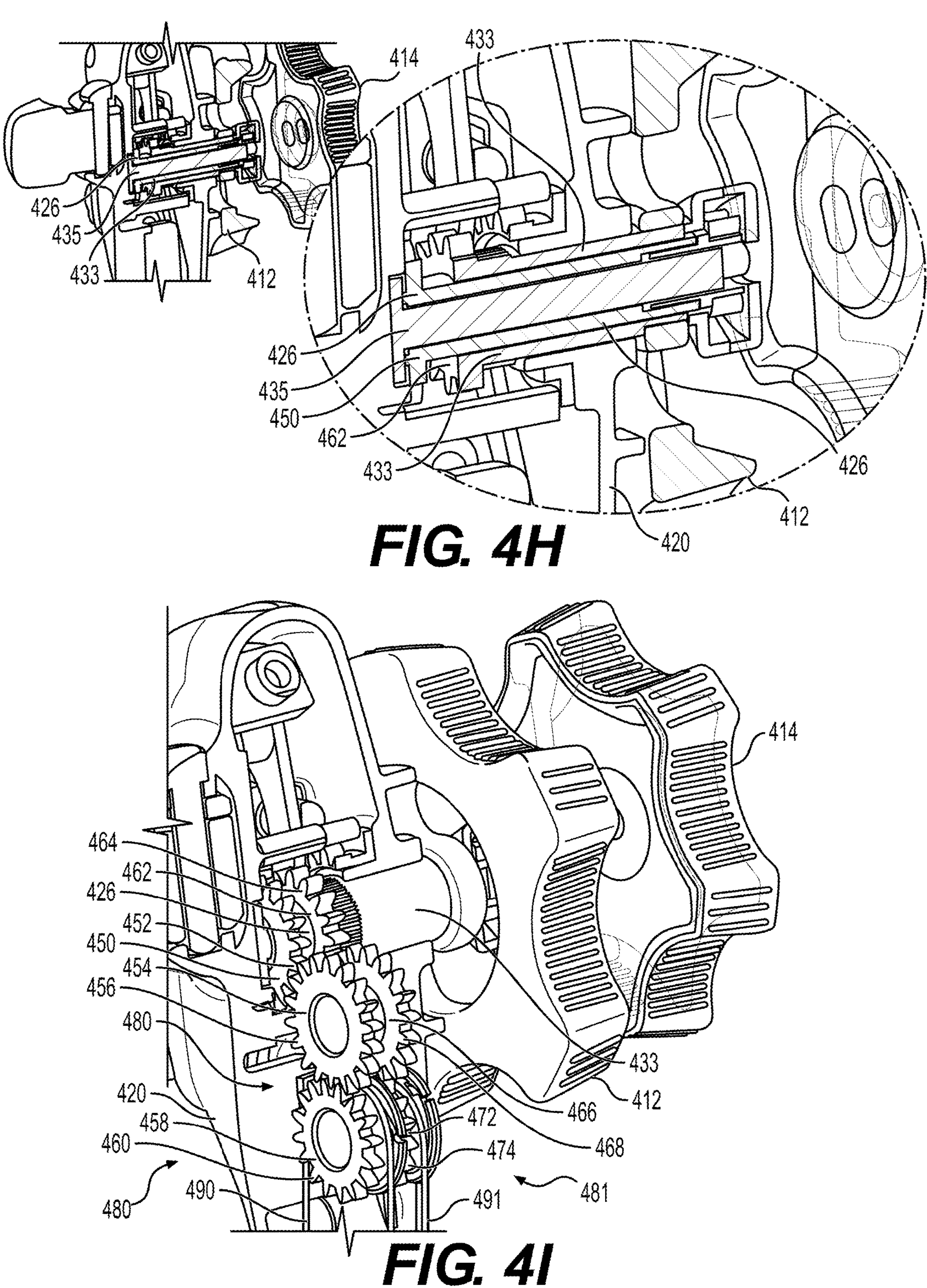
FIG. 4H is a magnified, cross-sectional view of the knob mechanism for the handle assembly in FIGS. 4A and 4B, according to aspects of this disclosure.
FIG. 4I is a perspective view of portions of the exemplary knob mechanism for the handle assembly in FIGS. 4A and 4B, with various portions removed to expose interior portions of the knob mechanism, according to aspects of this disclosure.
Figure 5E:
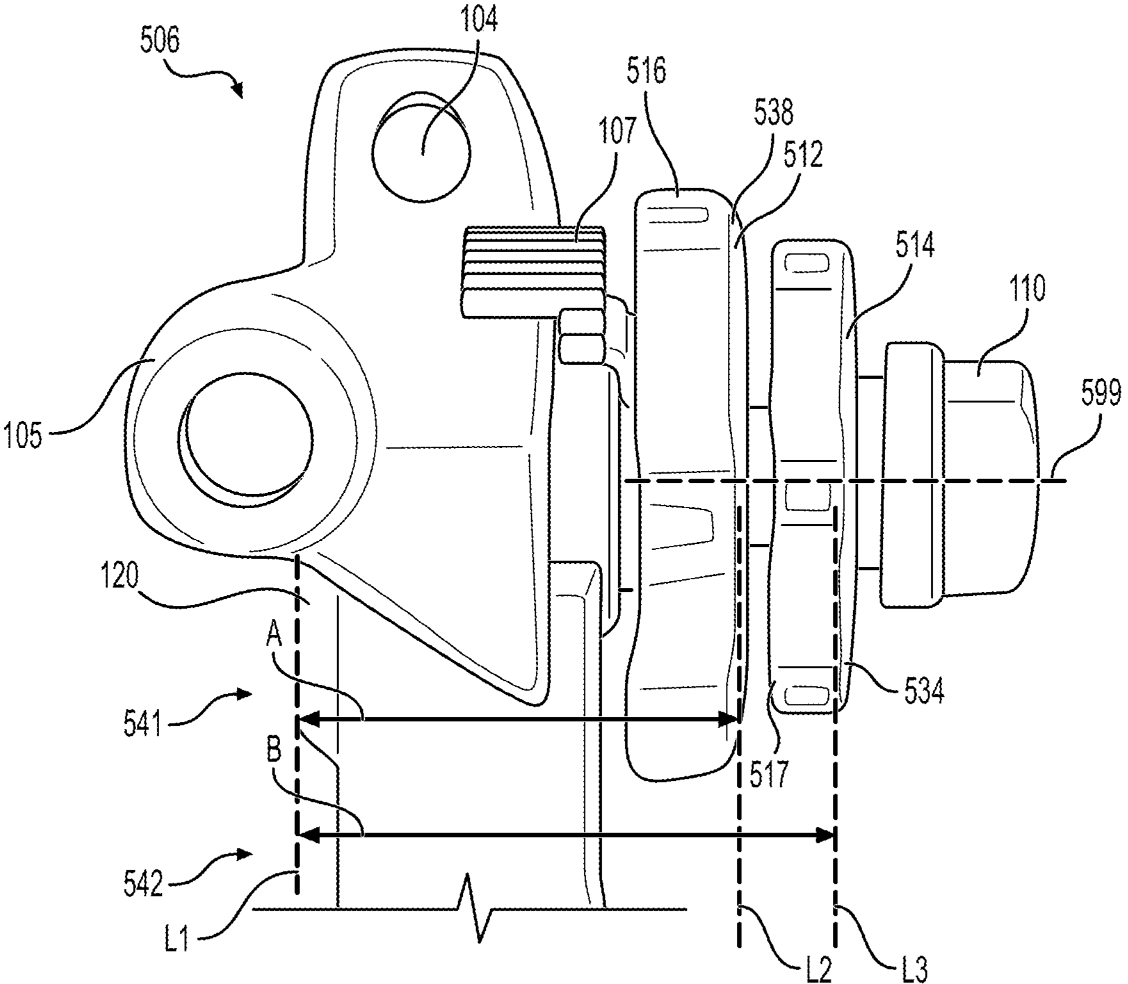
FIG. 5E is a side view of a proximal portion of a handle assembly, according to aspects of this disclosure.

Referring to FIGS. 4H and 4I, the first control knob 412 may be coupled to a fourth shaft 433 extending into the handle body 420 and to an internal gear assembly 481 within handle body 420. When a user rotates the first control knob 412, the fourth shaft 433 also rotates in order to move one or more actuation wires 491, for example, to deflect the distal tip 119 in the up or down direction. The second shaft 426 coupled to the second control knob 414, the fourth shaft 433 coupled to the first control knob 412, and a central, fifth shaft 435 are concentric. The fifth shaft 435 is fixed to the handle body 420. The fourth shaft 433 surrounds the second shaft 426 and the second shaft 426 surrounds the fifth shaft 435. The shafts 426 and 433 rotate about the rotational axis 391 independently of one another and relative to the shaft 435. For example, rotation of the first control knob 412 about the rotational axis 391 rotates the fourth shaft 433, but may not move the second shaft 426.

Referring to FIGS. 4C-4G, in operation, the gear mechanism 470 may provide a means for the second control knob 414 to rotate the shaft 426 in order to move one or more actuation wires 490, for example, to cause bending of an articulation section at a distal portion of an endoscope. When a user rotates the second control knob 414 clockwise, the first shaft 425 and the first gear 422 rotate clockwise and the teeth 440 engage the teeth 444 to rotate the idle gear 424 counterclockwise. When the idle gear 424 rotates counterclockwise, the teeth 444 engage the teeth 442 to rotate the second gear 423 clockwise. When the second gear 423 rotates clockwise, the shaft 426 also rotates clockwise to move one or more actuation wires 490. First gear 422 may not be directly engaged with second gear 423, and may be indirectly engaged with second gear 423 through idle gear 424.

The handle body 420 may include separate internal gear assemblies. For example, the gear assembly 480 associated with the first control knob 412, and the gear assembly 481 associated with the second control knob 414 (both shown in FIG. 4I). FIG. 4G shows handle body 420 with a portion of handle body removed to expose internal gear assembly 481. Internal gear assembly 482 is removed from FIG. 4G to more clearly show internal gear assembly 481. Referring to FIG. 4G, the internal gear assembly 481 for the second control knob 414 includes a fourth gear 450 with external teeth 452 coupled to the second shaft 426 and positioned within the handle body 420, a second idle gear 454 with external teeth 456, and a fifth gear 458 with external teeth 460. The second idle gear 454 is arranged between the fourth gear 450 and the fifth gear 458 so that external teeth 456 engage external teeth 452 and 460. The fifth gear 458 may be coupled to one or more actuation wires 490. As described above, as the second control knob 414 rotates clockwise, the second shaft 426 also rotates clockwise. As the second shaft 426 rotates clockwise, the fourth gear 450 also rotates clockwise. As the fourth gear 450 rotates clockwise, the external teeth 452 engage the external teeth 456 to rotate the second idle gear 454 counterclockwise. As the second idle gear 454 rotates counterclockwise, the external teeth 456 engage the external teeth 460 to rotate the fifth gear 458 clockwise, and thus move one or more actuation wires 490 to deflect the distal tip 119 in the left or right direction.

FIG. 4I illustrates a portion of handle assembly 406 with a portion of handle body 420 removed to expose internal gear assemblies 480, 481. Internal gear assembly 480 may be adjacent to internal gear assembly 481 within handle body 420. As shown in FIG. 4I, the internal gear assembly 480 coupled to the first control knob 412 may include a sixth gear 462 with external teeth 464 coupled to an end portion of the fourth shaft 433 internal to the handle body 420, a third idle gear 466 with external teeth 468, and a seventh gear 472 with external teeth 474. The gears 462, 466, and 472 may have similar structure and any of the features of gears 450, 454, and 458, respectively, and may be positioned adjacent to gears 450, 454, and 458, respectively. Each of gears 450, 454, 458, 462, 466, 472 may be rotatable coupled to an internal portion of handle body 420. As the first control knob 412 rotates clockwise, the shaft 433 and the sixth gear 462 rotate clockwise. As the sixth gear 462 rotates clockwise, the external teeth 464 engage the external teeth 468 to rotate the third idle gear 466 counterclockwise. As the third idle gear 466 rotates counterclockwise, the external teeth 468 engage the external teeth 474 to rotate the seventh gear 472 clockwise to move on or more actuation wires 491 to deflect the distal tip in the up or down direction.

In one example, the user's thumb 202 may apply a force to the second control knob 414 to rotate the second gear 423 clockwise or counter-clockwise to deflect the distal tip 119 in the left or right direction. In some examples, the user's thumb 202 may apply a force to the first control knob 412 to rotate to deflect the distal tip 119 in the up or down direction. Gear mechanism 470 provides a mechanism to offset the rotational axis of second knob 414 from the rotational axis of first knob 412.

FIGS. 5A-5D are perspective views of an exemplary first control knob 512 and an exemplary second control knob 514. The control knobs 512 and 514 may replace the control knobs 112 and 114 on handle body 120 (as shown in FIG. 5E). The control knobs 512, 514 include alternating radial protrusions 516, 517 and recesses 518, 519, respectively, circumferentially spaced from one another. The protrusions 516, 517 on the control knobs 512, 514, respectively, extend radially outward from a rotational knob axis 599. The number of protrusions 516, 517 and recesses 518, 519 of the control knobs 512, 514, respectively, may be five or any other suitable number. Each protrusion 516, 517 may include a tip portion 540, 541, respectively; and each tip portion 540, 541 may be positioned at a radially outermost portion of each protrusion 516, 517, respectively, relative to a rotational knob axis 599. Each tip portion 540, 541 may include a top surface 522, 530, respectively, facing radially outward from rotational knob axis 599, and a recessed portion 524, 532, respectively, recessed relative to top surface 522, 530, respectively. Recessed portions 524, 532 may improve gripping capabilities. The control knobs 512, 514 may include softened, curved surfaces along all the edges of the control knobs 512, 514, including side edges 525, 531 of tip portions 540, 541. Softened, curved edges 525, 531 may reduce a pinching and/or poking effect on the user's thumb 202 when operating first control knob 512 and/or second control knob 514. The control knobs 512, 514 may be made of plastic materials (ABS, PP, etc.), or any other suitable material that may provide softened surfaces. The control knobs 512, 514 include passages 521, 523, respectively, to assist with assembly of the control knobs 512, 514 on the handle body 120.

A first lateral surface 581 of first control knob 512 may be substantially planar and may extend across portions of each protrusion 516. First lateral surface 581 may face a direction away from handle body 120 when first control knob 512 is coupled to handle body 120. A second lateral surface 582 of second control knob 514 may be substantially planar and may be configured to be positioned adjacent to first lateral surface 581. By including first lateral surface 581 on first control knob 512 and second lateral surface 582 on second control knob 514, the second control knob 514 may be positioned close to the first control knob 512 on handle body 120, which may reduce the degree of abduction required by the user's thumb 202 to reach and/or operate the second control knob 514.

A depth of a protrusion is defined as a distance from (1) a midpoint of a curve extending from a side edge 525, 531 of a tip portion 540, 541 of a protrusion 516, 517 to an adjacent side edge 525, 531 of a tip portion 540, 541 of another protrusion 516, 517 to (2) a minimum of a recess 518, 519. A minimum of a recess 518, 519 may be the portion of recess 518, 519 closest to rotational axis 599. For example, as shown in FIG. 5B, the depth of the protrusion 516 is defined as a distance Y from (1) a midpoint of a curve 598 extending from the side edge 525 of the tip portion 540 of a protrusion 516 to the adjacent side edge 525 of the tip portion 540 of another protrusion 516 to (2) a minimum of the recess 518. A length between protrusions is defined as a distance from one side edge 525, 531 of the tip portion 540, 541 of one protrusion 516, 517 to the adjacent side edge 525, 531 of the tip portion 540, 541 of another protrusion 516, 517. For example, the length between protrusions 516 is defined as a distance X from one side edge 525 to the adjacent side edge 525 of an adjacent protrusion 516. The depth Y of each protrusion 516 and the length X between the protrusions 516 of the first control knob 512 may be approximately 13 millimeters and 32.00 millimeters, respectively. In some examples, the depth Y of each protrusion 516 the first control knob 512 may be between 1 millimeter and 30 millimeters (inclusive), and the length X between the protrusions 516 of the first control knob 512 may be between 1 millimeter millimeters (inclusive). This may provide additional surface area for the user's thumb 202 to move along and/or through the recess 518, while operating the first control knob 512 or the second control knob 514. In some examples, the depth Y of the protrusions 517 and the length X between the protrusions 517 may be approximately 9 millimeters and approximately 22 millimeters, respectively. This may provide narrower protrusions 517 on the second control knob 514, relative to the protrusions 516 of first knob 512, that may allow the user's thumb 202 to easily access both sides of the protrusions 517 during operation, such as to rotate the second control knob 514 clockwise or counterclockwise. In some examples, the depth Y of the protrusions 517 may be between approximately 1 millimeters and approximately 30 millimeters (inclusive). In some examples, the length X between the protrusions 517 may be between approximately 1 millimeters and approximately 30 millimeters (inclusive).

The diameter of the second control knob 514 may be approximately 58 millimeters, which may allow the second control knob 514 to be positioned closer to a user. In some examples, the diameter of the second control knob 514 may be between approximately 10 millimeters and approximately 30 millimeters (inclusive). A first side 586 outer surface 534 of the second control knob 514 may be convex away from the handle body 120, and a second side 587 outer surface 536 of the second control knob 514 may be flat. This flat outer surface 536 may allow for the second control knob 514 to be positioned closer to the first control knob 512, and thus closer to the handle body 120. In particular, the convex shape of the first side 586 outer surface 534 positions tip portions 541 of protrusions 517 closer to the handle body 120. The positioning of the control knobs 512, 514 closer to the handle body 120 reduces the distance the thumb 202 may need to travel to reach the control knobs 512, 514, and thus facilitates thumb 202 access to the control knobs 512, 514. For example, referring to FIG. 5E, a distance A from a point on an axis L1 defined along a first side 545 outer surface 542 of handle body 120 to a point on an axis L2 defined along the first lateral surface 581 of the first control knob 512 and substantially perpendicular to rotational knob axis 599, may be approximately 49 millimeters. In some examples, a distance A from a point on an axis L1 defined along a first side 545 outer surface 542 of handle body 120 to a point on an axis L2 defined along the first lateral surface 581 of the first control knob 512 and substantially perpendicular to rotational knob axis 599, may be between approximately millimeters and approximately 30 millimeters (inclusive). A distance B from a point on the axis L1 to a point on an axis L3 defined along the outer surface 534 of first side 586 of the second control knob 514 and substantially perpendicular to the rotational knob axis 599 is approximately 59 millimeters. By reducing the total width of the handle body 120 combined with first control knob 512 and second control knob 514, a user may more easily access first control knob 512 and second control knob 514 with the same hand that is holding handle body 120, for example because the reach required from the handle body 120 to first control knob 512 and second control knob 514 is reduced. In some examples, a distance B from a point on the axis L1 to a point on an axis L3 defined along the outer surface 534 of first side 586 of the second control knob 514 and substantially perpendicular to the rotational knob axis 599 may be between approximately 10 millimeters and approximately 30 millimeters (inclusive).

FIGS. 6A-6D are perspective views of an exemplary first control knob 612 and an exemplary second control knob 614. The control knobs 612 and 614 may replace the control knobs 112 and 114 on the handle body 120 (as shown in FIG. 6E). The control knobs 612, 614 include alternating radial protrusions 616, 617 and recesses 618, 619, respectively, circumferentially spaced from one another. Each of control knobs 612, 614 may have any of the features discussed herein in relation to control knobs 512, 514. Control knobs 612, 614 include tips 622, 623, respectively, with side edges 630, 631, respectively. Portions 624, 632 on outer surfaces of the tips 622, 623, respectively, may be recessed and may improve gripping capabilities. Portions 632 may each be a channel extending across tip 623. The control knobs 612, 614 may include softened, curved surfaces along all the edges of the protrusions 616, 617 of control knobs 612, 614, including the side edges 630, 631. Softened, curved edges may reduce a pinching and/or poking effect on the user's thumb 202 when operating the first control knob 612 and/or the second control knob 614, and may decrease strain on the user's thumb 202 during operation. Each control knob 612, 614 includes an opening 621, 625, respectively, to assist with assembly of the control knobs 612, 614 on the handle body 120.

The depth Y of each protrusion 616 may be approximately 12 millimeters, and the length X between adjacent pairs of protrusions 616 of the first control knob 612 may be approximately 32 millimeters. This may provide additional surface area for the user's thumb 202 to move along the recess 618 while operating the first control knob 612, and may provide additional surface area for the user's thumb 202 to move along the recess 619 while operating the second control knob 614. In some examples, the depth Y of each protrusion 616 may be between approximately 1 millimeter and approximately 30 millimeters (inclusive), and the length X between adjacent pairs of protrusions 616 of the first control knob 612 may be between approximately 1 millimeter and 30 millimeters (inclusive). The depth Y of protrusions 617 and the length X between protrusions 617 may be approximately 10 millimeters and approximately 22 millimeters, respectively. This may provide narrower protrusions 617 on the second control knob 614 that may allow the user's thumb 202 to easily access both sides of protrusions 617 to move the second control knob 614 upward or downward. In some examples, the depth Y of protrusions 617 may be between 1 millimeter and 30 millimeters (inclusive), and the length X between protrusions 617 may be between 1 millimeter and 30 millimeters (inclusive).

Figure 6E:
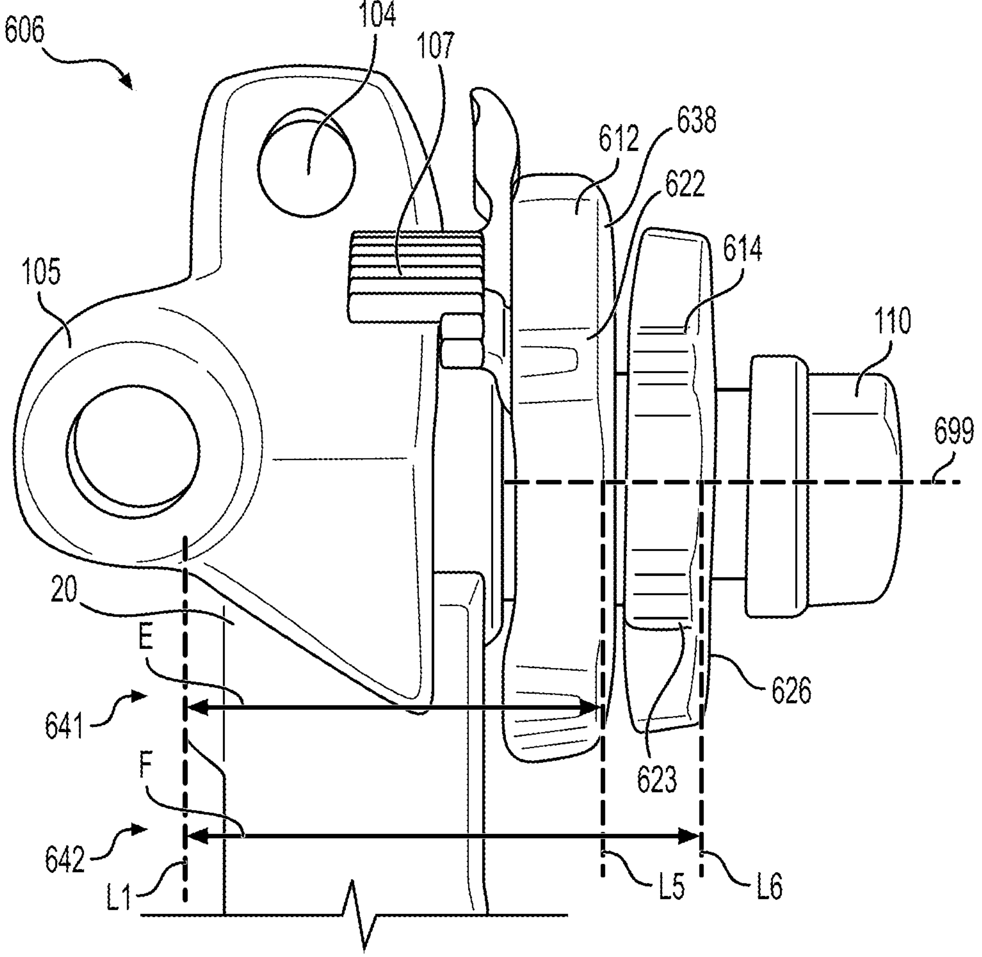
FIG. 6E is a side view of a proximal portion of a handle assembly, according to aspects of this disclosure.

A diameter of the second control knob 614 may be approximately 58 millimeters, which may position the second control knob 614 closer to a user on a handle assembly 606. In some examples, a diameter of the second control knob 614 may be between 25 millimeters and 60 millimeters (inclusive). A first outer surface 638 on a first side 660 of first control knob 612 may be a convex surface facing away from handle body 120, and a second outer surface 640 on a second side 661 of the first control knob 612 may be concave and may face towards the handle body 120. The curvature of first outer surface 638 and second outer surface 640 may position the first control knob 612, in particular, protrusions 616 closer to handle body 120. A first side 670 outer surface 626 of the second control knob 614 may be convex and may face away from the handle body 120. A second side 671 outer surface 628 of the second control knob 614 may be convex and may face towards the handle body 120 (as shown in FIG. 6E). Since outer surface 628 faces handle body 120 and is convex (e.g. curves away from handle body 120), this may reduce interference of the second control knob 614 when the user's thumb 202 is operating the first control knob 612 (e.g. due to the increased space between the control knobs 612, 614).

The positioning of the control knobs 612, 614 closer to the handle body 120 reduces the distance the thumb 202 may need to travel to reach the control knobs 612, 614 and thus allows for easier user thumb 202 accessibility to the control knobs 612, 614. For example, referring to handle assembly 606 of FIG. 6E, a distance F from a point on an axis L1 defined along a first side 641 outer surface 642 of handle body 120 to a point on an axis L6 defined along the outer surface 626 of the second control knob 614 and substantially perpendicular to rotational knob axis 699, may be approximately 60 millimeters. A distance E from a point on the axis L1 to a point on an axis L5 defined along the outer surface 638 of first side 660 of the first control knob 612 and substantially perpendicular to the rotational knob axis 699 may be approximately 49 millimeters. In some examples, a distance F from a point on an axis L1 defined along a first side 641 outer surface 642 of handle body 120 to a point on an axis L6 defined along the outer surface 626 of the second control knob 614 and substantially perpendicular to rotational knob axis 699, may be between 10 millimeters and 80 millimeters (inclusive); and a distance E from a point on the axis L1 to a point on an axis L5 defined along the outer surface 638 of first side 660 of the first control knob 612 and substantially perpendicular to the rotational knob axis 699 may be between approximately 5 millimeters and 100 millimeters (inclusive).

FIGS. 7A-7D are perspective views of an exemplary first control knob 712 and an exemplary second control knob 714. The control knobs 712 and 714 may replace the control knobs 112 and 114 on the handle body 120 (as shown in FIG. 7E), and may have any of the features described herein in relation to other control knobs 112, 114, 412, 414, 512, 514, 612, 614. The each of control knobs 712, 714 includes alternating radial protrusions 716, 717 and recesses 718, 719, respectively, circumferentially spaced from one another. The control knobs 712, 714 include tips 722, 724, respectively, with side edges 730, 731, respectively. Base edges 733, 735 of the tips 722, 724, respectively, may be wider than corresponding top edges 729, 740, respectively, of tips 722, 724, such that the radially outer facing surfaces 785, 786, relative to rotational knob axis 799, of the tips 722, 724 widen as the outer surfaces 785, 786 extend from the top edges 729, 740 to the base edges 733, 735, respectively. The outer surfaces 785 of tips 722 may be concave and include ribs 732 that may be arranged in a square shape. Each rib 732 may be a thin linear depression extending inward from adjacent portions having the ribs 732. The outer surfaces 786 of tips 724 may be concave and triangular in shape. The concave outer surfaces 785, 786 of tips 722, 724, and ribs 732 of tips 722 may provide proper thumb support and/or improve gripping capabilities.

The control knobs 712, 714 may include softened, curved surfaces along all the edges of the protrusions 716, 717, including the side edges 730, 731. Softened, curved edges may reduce a pinching and poking effect on the user's thumb 202 when operating the first control knob 712 and/or the second control knob 714. The control knobs 712, 714 include openings 721, 723, respectively, to assist with assembly of control knobs 712, 714 on handle body 120. The first control knob 712 may not include screw inserts typically found on the first control knob 112. This may allow the second control knob 714 to be positioned closer to the first control knob 712, which may reduce the degree of abduction required by the user's thumb 202 to reach and/or operate the second control knob 714.

The depth Y of each protrusion 716 and the length X between adjacent protrusions 716 of the first control knob 712 may be approximately 14 millimeters and approximately 29 millimeters, respectively. In some examples, depth Y of each protrusion 716 of the first control knob 712 may be between 5 millimeters and 50 millimeters (inclusive), and the length X between adjacent protrusions 716 of the first control knob 712 may be between 5 millimeters and 30 millimeters (inclusive). This may provide additional surface area for the user's thumb 202 to move along the recess 718, while operating the first control knob 612 or the second control knob 614. The depth Y of each protrusion 717 and the length X between adjacent protrusions 717 may be approximately 11 millimeters and approximately 23 millimeters, respectively. In some examples, the depth Y of each protrusion 717 may be between approximately 1 millimeter and approximately 50 millimeters (inclusive), and the length X between adjacent protrusions 717 may be between approximately 1 millimeter and approximately millimeters (inclusive). This may provide narrower protrusions 717 on the second control knob 714 that may allow the user's thumb 202 to easily access both sides of the protrusions 717 to move the second control knob 714 up or down. The smaller surface area of the narrower protrusions 717 may also be more accessible when a user's thumb 202 is extended.

The diameter of the second control knob 714 may be approximately 57 millimeters positioning the second control knob 714 closer to a user. In some examples, the diameter of the second control knob 714 may be between approximately millimeters and approximately 100 millimeters (inclusive). Outer surfaces 726, 736 may face away from handle body 120 and may be convex, positioning control knobs 712, 714, in particular protrusions 716, 717, closer to handle body 120. The positioning of the control knobs 712, 714 closer to handle body 120 reduces the distance the thumb 202 may need to travel to reach the control knobs 712, 714 and thus allows for easier user thumb 202 accessibility to the control knobs 712, 714.

Figure 7E:
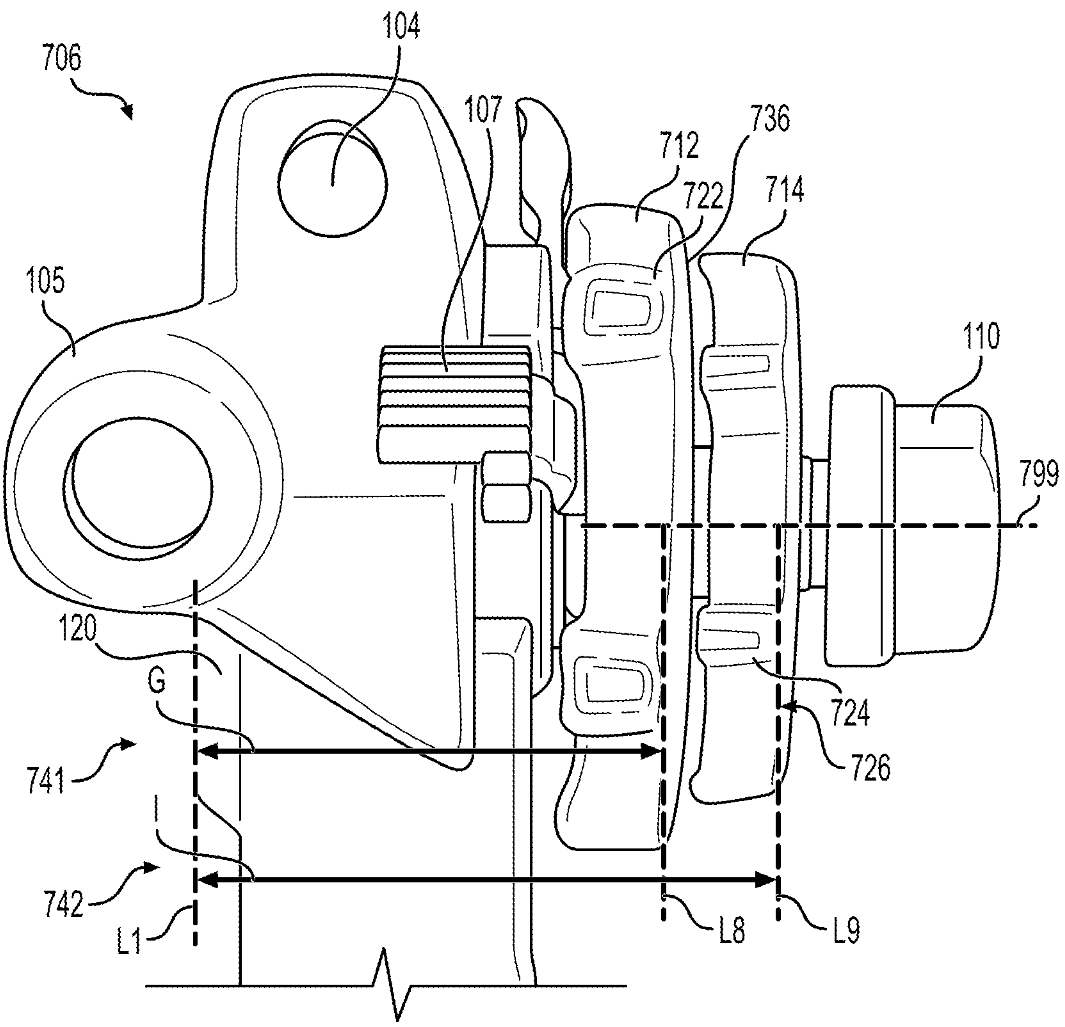
FIG. 7E is a side view of a proximal portion of a handle assembly, according to aspects of this disclosure.

For example, referring to handle assembly 706 of FIG. 7E, a distance I from a point on an axis L1 defined along a first side 741 outer surface 742 of handle body 120 to a point on an axis L9 defined along the outer surface 726 of the second control knob 714 and substantially perpendicular to rotational knob axis 799, may be approximately 59 millimeters. A distance G from a point on the axis L1 to a point on an axis L8 defined along the outer surface 736 of the first control knob 712 and substantially perpendicular to the rotational knob axis 799 may be approximately 47 millimeters. In some examples, a distance I from a point on an axis L1 defined along a first side 741 outer surface 742 of handle body 120 to a point on an axis L9 defined along the outer surface 726 of the second control knob 714 and substantially perpendicular to rotational knob axis 799, may be between 20 millimeters and 100 millimeters (inclusive). In some examples, a distance G from a point on the axis L1 to a point on an axis L8 defined along the outer surface 736 of the first control knob 712 and substantially perpendicular to the rotational knob axis 799 may be between 1 millimeter and 100 millimeters (inclusive).

FIGS. 8A-8D are perspective views of an exemplary first control knob 812 and an exemplary second control knob 814. Control knobs 812, 814 may have any of the features discussed herein in relation to control knobs 112, 114, 412, 414, 512, 514, 612, 614,712, 714. The control knobs 812 and 814 may replace the control knobs 112 and 114 on handle body 120 (as shown in handle assembly 806 in FIG. 8E). The control knobs 812, 814 include alternating radial protrusions 816, 817 and recesses 818, 819, respectively, circumferentially spaced from one another. The protrusions 816, 817 of the control knobs 812, 814 extend radially outward from a rotational knob axis 899. The control knobs 812, 814 include tips 822, 824, respectively, with side edges 825, 831. Outer surfaces 881, 882 of tips 822 and 824 may include grip projections 832 and 844 to improve gripping capabilities. Each grip projection 832, 844 protrudes from adjacent portions of the outer surface 881, 882. Each grip projection 832, 844 is oval shaped and may have a central longitudinal axis substantially parallel to each adjacent grip projection 832, 844. The control knobs 812 and 814 includes openings 821 and 823, respectively, to assist with assembly of the control knobs 812, 814 on the handle body 120. The first control knob 812 may not include screw inserts typically found on the first control knob 112. This may allow the second control knob 814 to be positioned closer to the first control knob 812, which may reduce the degree of abduction required by the user's thumb 202 to reach and/or operate the second control knob 814.

The depth Y of each protrusion 816 and the length X between adjacent protrusions 816 of the first control knob 812 may be approximately 14 millimeters and approximately 31 millimeters, respectively. In some examples, the depth Y of each protrusion 816 may be between 1 millimeter and 30 millimeters (inclusive). In some examples, the length X between adjacent protrusions 816 may be between 1 millimeter and 70 millimeters (inclusive). This may provide additional surface area for the user's thumb 202 to move along the recess 818, while operating the first control knob 812 or the second control knob 814. The depth Y of the protrusions 817 and the length X between adjacent protrusions 817 may be approximately 8 millimeters and approximately 21 millimeters, respectively. In some examples, the depth Y of the protrusions 817 may be between 1 millimeter and 50 millimeters (inclusive) and the length X between adjacent protrusions 817 may be between 5 millimeters and 30 millimeters (inclusive). This may provide narrower protrusions 817 on the second control knob 814 that may allow the user's thumb 202 to easily access both sides of the protrusions 817 to move the second control knob 814 up or down. The narrower protrusions 817 may facilitate operation of second control knob 814 with an extended thumb 202.

A diameter of the second control knob 814 may be approximately 60 millimeters, which may position the second control knob 814 closer to a user. In some examples, the diameter of the second control knob 814 may be between 10 millimeters and 100 millimeters (inclusive). Protrusions 816, 817 may curve towards handle body 120 to position protrusions 816, 817 closer to the handle body 120. The second control knob 814 may be thicker than the typical second control knob 114 to provide additional support for the user's thumb 202 and additional surface area for the user to place the thumb 202 on the outer surfaces of the tips 824 during operation of the second control knob 814. For example, the width, measured along rotational knob axis 899, of second control knob 814 may be approximately 10 millimeters or approximately 12 millimeters. In some examples, the width, measured along rotational knob axis 899, of second control knob 814 may be between 1 millimeter and 30 millimeters.

Figure 8A:
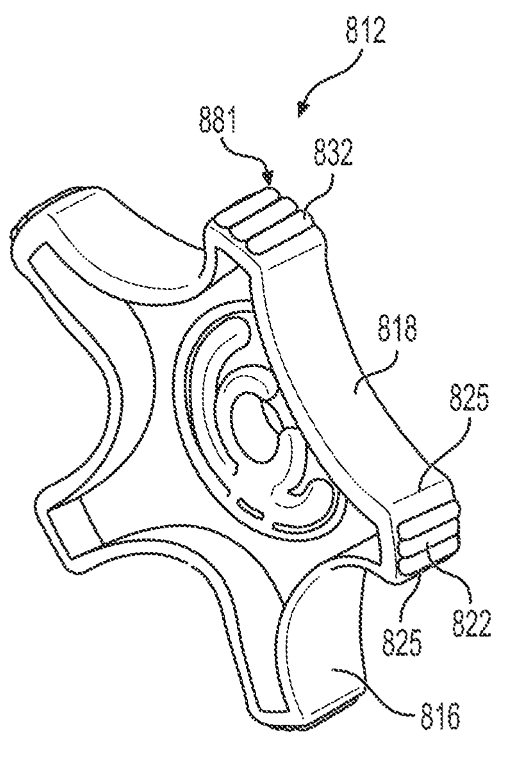
FIGS. 8A-8D are perspective views of exemplary control knobs, according to aspects of this disclosure.
Figure 8B:
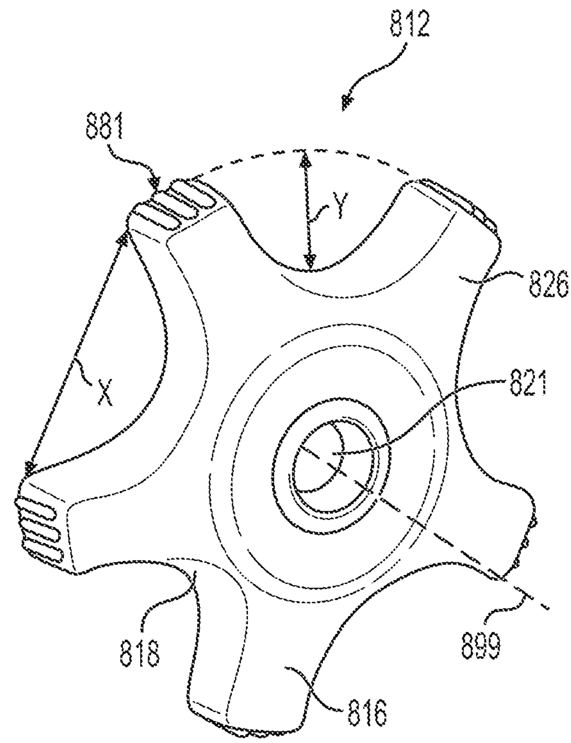
Figure 8C:
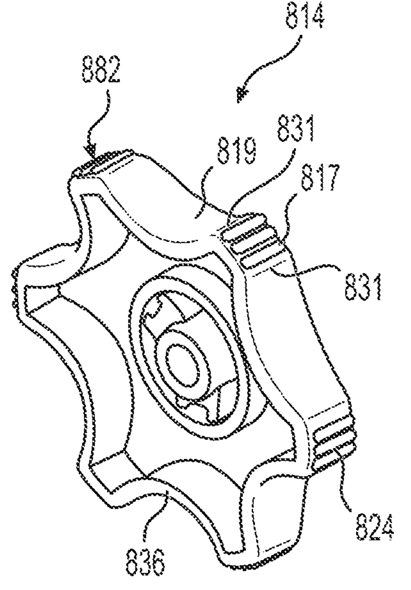
Figure 8D:
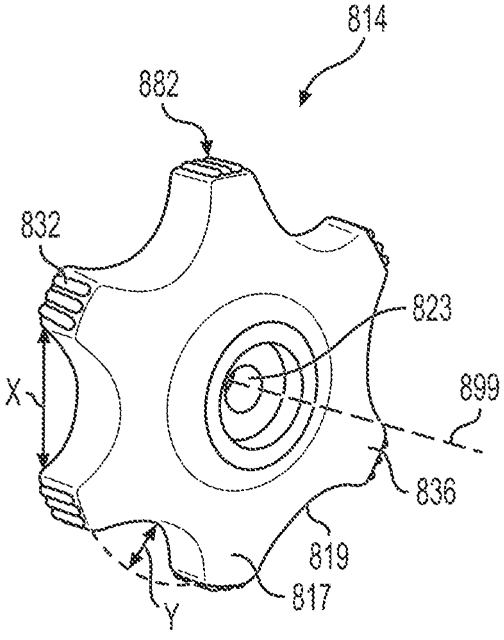
Figure 8E:
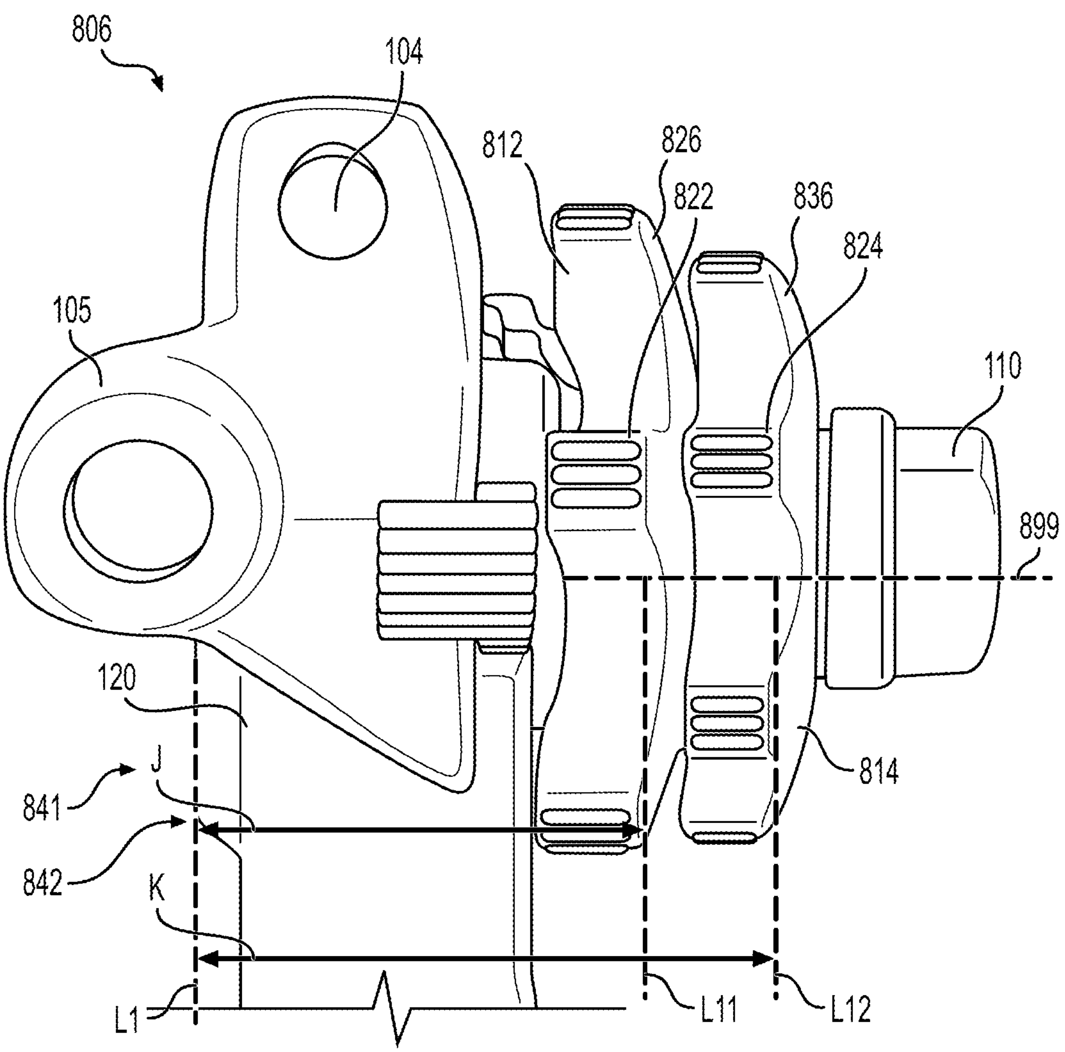
FIG. 8E is a side view of a proximal portion of a handle assembly, according to aspects of this disclosure.

For example, referring to handle assembly 806 of FIG. 8E, a distance K from a point on an axis L1 defined along a first side 841 outer surface 842 of handle body 120 to a point on an axis L12 defined along the outer surface 836 of the second control knob 814 and substantially perpendicular to rotational knob axis 899, may be approximately 59 millimeters. In some examples, a distance K from a point on an axis L1 defined along a first side 841 outer surface 842 of handle body 120 to a point on an axis L12 defined along the outer surface 836 of the second control knob 814 and substantially perpendicular to rotational knob axis 899, may be between 10 millimeters and 100 millimeters (inclusive). A distance J from a point on the axis L1 to a point on an axis L11 defined along the outer surface 826 of the first control knob 812 and substantially perpendicular to the rotational knob axis 899 may be approximately 46 millimeters. In some examples, a distance J from a point on the axis L1 to a point on an axis L11 defined along the outer surface 826 of the first control knob 812 and substantially perpendicular to the rotational knob axis 899 may be between 5 millimeters and 80 millimeters (inclusive).

The handle assemblies 406, 506, 606, 706, 806 and control knobs 412, 414, 512, 514, 612, 614, 712, 714, 812, 814 of this disclosure may assist with ergonomically positioning fingers of the user when the user operates endoscope 101 or other medical devices, may reduce hand strain caused by excessive movement and/or reaching of fingers when the user operates endoscope 101, and may reduce the chance of the user losing his or her grip. Also, the handle assemblies 406, 506, 606, 706, 806 and control knobs 412, 414, 512, 514, 612, 614, 712, 714, 812, 814 may help prevent repeated repositioning of a user's hand on a medical device handle due to fatigue, strain, or other difficulty. Each of the aforementioned handle assemblies 406, 506, 606, 706, 806 and control knobs 412, 414, 512, 514, 612, 614, 712, 714, 812, 814, whether used in conjunction with an endoscope system or any other medical device, may be used to enhance and/or facilitate a user's grip on a handle and/or enhance operation of a handle assembly. Any portion of the handle assembly or control knobs discussed herein may be incorporated into a handle of an endoscope or other medical device to improve a user's operation of the device. The handle assemblies 406, 506, 606, 706, 806 and the control knobs 412, 414, 512, 514, 612, 614, 712, 714, 812, 814 of this disclosure may allow multiple users with different size hands and/or fingers to comfortably use the same handle assembly. Any of the features discussed in relation to any of the handle assemblies 406, 506, 606, 706, 806 and control knobs 412, 414, 512, 514, 612, 614, 712, 714, 812, 814 may be incorporated into any other example of a handle assembly 406, 506, 606, 706, 806 and control knob 412, 414, 512, 514, 612, 614, 712, 714, 812, 814.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and embodiments be considered as exemplary only.

We claim:

1. A handle assembly for a medical device, the handle assembly comprising:

a handle body;

a first knob for controlling movement of a distal portion of the medical device, the first knob rotatable about a first rotational axis, wherein a radially outermost surface of the first knob tapers relative to the first rotational axis in a first direction; and a second knob for controlling movement of the distal portion of the medical device, the second knob rotatable about a second rotational axis, wherein a radially outermost surface of the second knob tapers relative to the second rotational axis in a second direction, wherein the first rotational axis is offset from the second rotational axis.

2. The handle assembly of claim 1, wherein the first knob includes grip protrusions extending radially outward, relative to the first rotational axis, from a radially outward facing surface of the first knob.

3. The handle assembly of claim 1, wherein the first rotational axis is substantially parallel to the second rotational axis.

4. The handle assembly of claim 1, wherein the handle assembly further comprises a first gearing assembly configured to rotate a first actuation shaft around the second rotational axis when the second knob rotates about the second rotational axis, wherein the first actuation shaft is offset from the first rotational axis.

5. The handle assembly of claim 4, wherein the first gearing assembly is contained within a casing positioned between the first knob and the second knob.

6. The handle assembly of claim 4, wherein the first gearing assembly includes a first gear fixedly coupled to the second knob and fixedly coupled to the first actuation shaft.

7. The handle assembly of claim 6, wherein the first gearing assembly further comprises a second actuation shaft fixedly coupled to a second gear and configured to rotate about the first rotational axis when the second knob rotates.

8. The handle assembly of claim 7, wherein the second actuation shaft is coupled to a second gearing assembly internal to the handle body, wherein the second gearing assembly includes a fourth gear coupled to the second actuation shaft, a fifth gear coupled to an actuation wire, and a sixth gear engaged with the fourth gear and the fifth gear.

9. The handle assembly of claim 7, wherein the second actuation shaft is offset from the second rotational axis.

10. The handle assembly of claim 1, wherein the second rotational axis is spaced approximately ten millimeters from the first rotational axis.

11. The handle assembly of claim 1, wherein the handle body includes a first side and a second side opposite from the first side, wherein each of the first knob and the second knob is positioned on the first side.

12. The handle assembly of claim 11, wherein the first knob is positioned between the first side of the handle body and the second knob.

13. The handle assembly of claim 1, wherein the first knob includes a series of radial protrusions, and each radial protrusion includes a recessed portion at a tip of the respective radial protrusion.

14. The handle assembly of claim 1, further comprising a support member extending longitudinally from the handle body, wherein the second knob is positioned on a distal end of the support member.

15. The handle assembly of claim 14, wherein the first knob comprises an opening, and wherein the support member extends through the opening of the first knob.

* * * * *